(12) United States Patent
Kandavilli et al.

(10) Patent No.: US 11,179,465 B2
(45) Date of Patent: *Nov. 23, 2021

(54) TOPICAL COMPOSITIONS COMPRISING A CORTICOSTEROID

(71) Applicant: PRIMUS PHARMACEUTICALS, INC., Scottsdale, AZ (US)

(72) Inventors: Sateesh Kandavilli, Plainsboro, NJ (US); Madhusudhan Bommagani, Hyderabad (IN); Vijendra Nalamothu, Basking Ridge, NJ (US); Franklin Okumu, Morristown, NJ (US)

(73) Assignee: Primus Pharmaceuticals, Inc., Scottsdale, AZ (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/820,601

(22) Filed: Nov. 22, 2017

(65) Prior Publication Data

US 2018/0078643 A1    Mar. 22, 2018

Related U.S. Application Data

(63) Continuation of application No. 15/068,428, filed on Mar. 11, 2016, now Pat. No. 9,855,334, which is a continuation-in-part of application No. 14/645,297, filed on Mar. 11, 2015, now abandoned.

(60) Provisional application No. 61/951,188, filed on Mar. 11, 2014.

(51) Int. Cl.
| | |
|---|---|
| *A61K 47/06* | (2006.01) |
| *A61K 9/14* | (2006.01) |
| *A61K 9/06* | (2006.01) |
| *A61K 9/107* | (2006.01) |
| *A61K 31/573* | (2006.01) |
| *A61K 47/10* | (2017.01) |
| *A61K 47/44* | (2017.01) |
| *A61K 9/00* | (2006.01) |

(52) U.S. Cl.
CPC ............ *A61K 47/06* (2013.01); *A61K 9/0014* (2013.01); *A61K 9/06* (2013.01); *A61K 9/107* (2013.01); *A61K 31/573* (2013.01); *A61K 47/10* (2013.01); *A61K 47/44* (2013.01)

(58) Field of Classification Search
CPC ........ A61K 47/06; A61K 9/0014; A61K 9/06; A61K 9/107; A61K 31/573; A61K 47/10; A61K 47/44
See application file for complete search history.

(56) References Cited

U.S. PATENT DOCUMENTS

| | | |
|---|---|---|
| 3,892,856 A | 7/1975 | Hill et al. |
| 3,934,013 A | 1/1976 | Poulsen |
| 4,053,089 A | 10/1977 | Gamadia |
| 4,343,798 A | 8/1982 | Fawzi |
| 4,552,872 A | 11/1985 | Cooper et al. |
| 5,068,099 A | 11/1991 | Sramek |
| 5,369,131 A | 11/1994 | Poli et al. |
| 5,422,361 A | 6/1995 | Munayyer et al. |
| 5,622,286 A | 4/1997 | Renault |
| 5,874,074 A | 2/1999 | Smith |
| 5,958,379 A | 9/1999 | Regenold et al. |
| 5,972,920 A | 10/1999 | Seidel |
| 5,976,555 A | 11/1999 | Liu et al. |
| 6,075,056 A | 6/2000 | Quigley, Jr. et al. |
| 6,126,920 A | 10/2000 | Jones et al. |
| 6,158,617 A | 12/2000 | Hershey et al. |
| 6,284,234 B1 | 9/2001 | Niemiec et al. |
| 6,294,186 B1 | 9/2001 | Beerse et al. |
| 6,387,383 B1 | 5/2002 | Dow et al. |
| 6,419,913 B1 | 7/2002 | Niemiec et al. |
| 6,432,415 B1 | 8/2002 | Osborne et al. |
| 6,479,058 B1 | 11/2002 | McCadden |
| 6,579,512 B2 | 6/2003 | Crutchfield, III |
| 6,656,928 B1 | 12/2003 | McCadden |
| 6,946,120 B2 | 9/2005 | So et al. |
| 6,962,691 B1 | 11/2005 | Lulla et al. |
| 7,029,694 B2 | 4/2006 | Ebert et al. |
| 7,078,049 B2 | 7/2006 | Senee |
| 7,078,058 B2 | 7/2006 | Jones et al. |
| 7,316,810 B1 | 1/2008 | Preuilh et al. |
| 7,341,208 B2 | 3/2008 | Peters et al. |
| 7,393,548 B2 | 7/2008 | Friedman |
| 9,364,485 B2 | 6/2016 | Ubaidulla et al. |
| 9,433,630 B1 | 9/2016 | Ubaidulla et al. |
| 9,439,911 B2 | 9/2016 | Ubaidulla et al. |
| 9,655,907 B2 | 5/2017 | Ubaidulla et al. |
| 9,775,851 B1 | 10/2017 | Ubaidulla et al. |
| 9,855,334 B2 | 1/2018 | Kandavilli et al. |
| 9,877,974 B2 | 1/2018 | Ubaidulla et al. |

(Continued)

FOREIGN PATENT DOCUMENTS

| | | |
|---|---|---|
| CN | 102526070 A | 7/2012 |
| EP | 0437131 A1 | 7/1991 |

(Continued)

OTHER PUBLICATIONS

Eurasian Patent Organization, Office Action issued in corresponding Application No. 201691808, dated Aug. 30, 2017.
New Zealand Intellectual Property Office, First Examination Report issued in corresponding Application No. 724925, dated Sep. 8, 2017.
International Search Report and Written Opinion issued in PCT/US2015/049244, dated Aug. 15, 2015.
International Search Report and Written Opinion for Application No. PCT/US2015/020031 dated Jun. 17, 2015.
Guidance for industry; Topical dermatological corticosteroids: in vivo Bioequivalence; Dated Jun. 2, 1995.
Sintov, et al., "Transdermal Drug Delivery Using Microemulsion and Aqueous Systems: Influence of Skin Storage Conditions on the in Vitro Permeability of Diclofenac from Aqueous Vehicle System," 311 Int. J. Pharm , pp. 55-62. 2006).

(Continued)

*Primary Examiner* — Jared Barsky
(74) *Attorney, Agent, or Firm* — Troutman Pepper Hamilton Sanders LLP

(57) ABSTRACT

Topical compositions comprising a corticosteroid, at least one alcohol, and a penetration enhancing agent.

15 Claims, 4 Drawing Sheets

(56) References Cited

U.S. PATENT DOCUMENTS

| | | | |
|---|---|---|---|
| 9,956,231 | B1 | 5/2018 | Ubaidulla et al. |
| 10,064,875 | B2 | 9/2018 | Ubaidulla et al. |
| 10,179,137 | B2 | 1/2019 | Ubaidulla et al. |
| 10,588,914 | B2 | 3/2020 | Ubaidulla et al. |
| 10,905,697 | B2 | 2/2021 | Ubaidulla et al. |
| 2003/0118528 | A1 | 6/2003 | Walters et al. |
| 2003/0203407 | A1 | 10/2003 | Craig et al. |
| 2004/0258701 | A1 | 12/2004 | Dominowski et al. |
| 2005/0031692 | A1 | 2/2005 | Beyerinck et al. |
| 2005/0281754 | A1 | 12/2005 | Willcox et al. |
| 2006/0018937 | A1 | 1/2006 | Friedman et al. |
| 2006/0057168 | A1* | 3/2006 | Larm ............... A61K 8/062 424/400 |
| 2006/0099173 | A1 | 5/2006 | Puglia et al. |
| 2006/0147383 | A1 | 7/2006 | Mallard et al. |
| 2006/0239929 | A1 | 10/2006 | Dow et al. |
| 2006/0246098 | A1 | 11/2006 | Rao et al. |
| 2007/0020299 | A1 | 1/2007 | Pipkin et al. |
| 2007/0049518 | A1* | 3/2007 | Chandler ............ A61K 31/00 514/615 |
| 2007/0140993 | A1 | 6/2007 | Evison |
| 2007/0142343 | A1 | 6/2007 | Gans et al. |
| 2007/0164129 | A1 | 7/2007 | Doner et al. |
| 2007/0189977 | A1 | 8/2007 | Zhang et al. |
| 2007/0190019 | A1 | 8/2007 | Guo et al. |
| 2007/0243132 | A1 | 10/2007 | Russell-Jones et al. |
| 2008/0003208 | A1 | 1/2008 | Nivaggioli |
| 2008/0102039 | A1 | 5/2008 | Tickle |
| 2008/0118453 | A1 | 5/2008 | Mallard et al. |
| 2008/0166303 | A1 | 7/2008 | Tamarkin et al. |
| 2008/0206155 | A1 | 8/2008 | Tamarkin et al. |
| 2008/0206161 | A1 | 8/2008 | Tamarkin et al. |
| 2008/0206170 | A1 | 8/2008 | Nivaggioli et al. |
| 2008/0207570 | A1* | 8/2008 | Segura-Orsoni ..... A61K 9/0014 514/168 |
| 2008/0275014 | A1 | 10/2008 | Yamamoto et al. |
| 2008/0300229 | A1 | 12/2008 | Willcox et al. |
| 2009/0035375 | A1 | 2/2009 | Skrtic et al. |
| 2009/0041680 | A1 | 2/2009 | Tamarkin et al. |
| 2009/0053290 | A1 | 2/2009 | Sand et al. |
| 2009/0093547 | A1 | 4/2009 | Corbitt et al. |
| 2009/0098069 | A1 | 4/2009 | Vacca |
| 2009/0104131 | A1 | 4/2009 | Segura-Orsoni et al. |
| 2009/0104132 | A1 | 4/2009 | Segura-Orsoni et al. |
| 2009/0130029 | A1 | 5/2009 | Tamarkin et al. |
| 2009/0181080 | A1 | 7/2009 | Kottayil et al. |
| 2010/0221194 | A1 | 9/2010 | Loupenok |
| 2010/0240621 | A1 | 9/2010 | Sen et al. |
| 2010/0249060 | A1 | 9/2010 | Smith |
| 2010/0278759 | A1 | 11/2010 | Murad |
| 2011/0305643 | A1 | 12/2011 | Gurge et al. |
| 2012/0214776 | A1* | 8/2012 | Ubaidulla ............ A61K 9/0014 514/174 |
| 2012/0238535 | A1 | 9/2012 | Smith |
| 2012/0301511 | A1 | 11/2012 | Criscione |
| 2013/0028850 | A1 | 1/2013 | Tamarkin et al. |
| 2014/0274982 | A1 | 9/2014 | Bakan et al. |
| 2014/0357607 | A1* | 12/2014 | Lathrop ................ A61K 47/14 514/172 |
| 2016/0030450 | A1 | 2/2016 | Kandavalli et al. |
| 2016/0184431 | A1 | 6/2016 | Kandavalli et al. |
| 2016/0199493 | A1 | 7/2016 | Kandavalli et al. |
| 2016/0235767 | A1 | 8/2016 | Ubaidulla et al. |
| 2016/0235768 | A1 | 8/2016 | Ubaidulla et al. |
| 2016/0361325 | A1 | 12/2016 | Ubaidulla et al. |
| 2017/0258813 | A1 | 9/2017 | Ubaidulla et al. |
| 2017/0360808 | A1 | 12/2017 | Ubaidulla et al. |
| 2018/0104260 | A1 | 4/2018 | Ubaidulla et al. |
| 2018/0207178 | A1 | 7/2018 | Ubaidulla et al. |
| 2018/0250312 | A1 | 9/2018 | Kandavilli et al. |
| 2018/0338986 | A1 | 11/2018 | Ubaidulla et al. |
| 2019/0175735 | A1 | 6/2019 | Kandavilli et al. |
| 2019/0209584 | A1 | 7/2019 | Ubaidulla et al. |
| 2020/0230155 | A1 | 7/2020 | Kandavilli et al. |

FOREIGN PATENT DOCUMENTS

| | | | | |
|---|---|---|---|---|
| EP | 1386670 | A2 | 2/2004 | |
| EP | 2473161 | A2 | 7/2012 | |
| WO | 2006/005845 | A1 | 1/2006 | |
| WO | 2006003481 | A2 | 1/2006 | |
| WO | 2006102004 | A2 | 9/2006 | |
| WO | 2006/115987 | A2 | 11/2006 | |
| WO | 20060115987 | A2 | 11/2006 | |
| WO | 2007094605 | A1 | 8/2007 | |
| WO | 2007133731 | A2 | 11/2007 | |
| WO | 2009003199 | A1 | 12/2008 | |
| WO | 2009015456 | A1 | 2/2009 | |
| WO | 2009063493 | A2 | 5/2009 | |
| WO | 2011/026076 | A2 | 3/2011 | |
| WO | WO 2011026076 | A2 * | 3/2011 | .......... A61K 9/0014 |
| WO | 2012/053007 | A1 | 4/2012 | |
| WO | 2014/197398 | | 12/2014 | |
| WO | 2016145407 | A1 | 9/2016 | |

OTHER PUBLICATIONS

Boonme, Prapapom, "Applications of Microemulsions in Cosmetics" 6 J. Cosmetic Dermatology pp. 223-228 (2007).

Akhter, et al., "Investigation of Nanoemulsion System for Transdermal Delivery of Domeperidone: Ex-vivo and in-vivo Studies," 4 Current Nanoscience, pp. 381-390 (2008).

Housman, et al., "Patients with Psoriasis Prefer Solution and Foam Vehicles: A Quantitative Assessment of Vehicle Preference," Cutis 70(6): pp. 327-332 (2002).

Purdon, et al., "Foam Drug Delivery in Dermatology," Am. J. Drug. Deliv. 1(1): pp. 71-75 (2003).

Mraz, et al., "Different treatment outcomes with different formulations of clobetasol propionate 0.05% for the treatment of plaque psoriasis," Journal of Dermatological Treatment 2008; 19: pp. 354-359.

Panchagnula et al., Development and Evaluation of an Intracutaneous Depot Formulation of Corticosteroids Using Transcutol as a Cosolvent: In-vitro, Ex-Vivo and In-vivo rat Studies. J Pharm Pharmacol, Jan. 16, 1991; 43(9):609-614.

Ritschel et al., Development of an Intracutaneous Depot for Drugs: Binding, Drug Accumulation, and Retention Studies, and Mechanism of Depot. Skin Pharmacol. 1991;4(4):235-245.

Osborne, D.W., Diethylene glycol monoethyl ether: an emerging solvent in topical dermatology products, Journal of Cosmetic Dermatology, 2011;10:324-329.

New Zealand Intellectual Property Office, First Examination Report issued in corresponding Application No. 735341, dated May 4, 2018.

IP Australia, Examination Report No. 1 issued in corresponding Application No. 269179, dated May 11, 2018.

European Patent Office, Examination Report issued in corresponding Application No. 16712608.5, dated Aug. 20, 2018.

Eurasian Patent Office, Office Action issued in corresponding Application No. 201791921, dated Oct. 22, 2018. Translation not available.

Badilli, U. et al. Microparticulate Based Topical Delivery System of Clobetasol Propionate AAPS PharmSciTech, vol. 12, No. 3, Sep. 2011 (#2011) DOI: 10.1208/s12249-011-9661-7.

Blanken, R, et al. Effect of mineral oil and linoleic-acid-containing emulsions on the skin vapour loss of sodiumauryi-sulphate-induced irritant skin reactions, Contact Dermatitis 1989: 20: 93-97.

Campisi, G et al., A new delivery system of clobetasol-17-propionate (lipid-loaded microspheres 0.025%) compared with a conventional formulation (lipophilic ointment in a hydrophilic phase 0.025%) in topical treatment of atrophic/erosive oral lichen planus. A Phase IV, randomized, observer-blinded, parallel group clinical trial, Br J Dermatol. Department of Chemistry and Pharmaceutical Technologies, University of Palermo, Palermo, Italy. May 2004;150(5):984-90.

Dang, HV., et al_ Composition analysis of two batches of polysorbate 60 using MS and NMR techniques, Journal of Pharmaceutical and Biomedical Analysis 40 (2006): 1155-1165.

(56) References Cited

OTHER PUBLICATIONS

"Diprolene-betamethasone dipropionate lotion", Jan. 1, 2004 (Jan. 1, 2004), pp. 1-5, Retrieved from the Internet: URL:http://dailymed.nlm.nih.gov/dailymed/druginfo.cfm?id: :65178 [retrieved on Aug. 13, 2014).
European Patent Office, international Search Report issued in corresponding Application No. PCT/US2016/022194, dated Jul. 22, 2016 (WO2016145407).
Extended European Search Report for Application No. 10812737.4 dated Aug. 1, 2012. (WO2011026076).
Fini, A. et al., "Control ofTransdermal Permeation of Hydrocortisone Acetate from Hydrophilic and Lipophilic Formulations", AAPS PhramSciTech, Sep. 3, 2008, pp. 762-768, vol. 9—Issue No. 3.
International Search Report and Written Opinion for PCT/ US2010/ 047240 dated May 23, 2011.
Lachenmeier, "Safety evaluation of topical applications of ethanol on the skin and inside the oral cavity," J Occup Med Toxicol. 2008; 3: 26. See https://www.ncbi.nlm.nih.gov/pmc/articles/PMC2596158/.
Patzelt, A, et al. In vivo investigations on the penetration of various oils and their influence on the skin barrier, Skin Research and Technology 2011: 0:1-6.
Product Description—Clobetasol propionate gel label (Jan. 2008) Perrigo Website.
Product Description—Temovate E label (Aug. 2002), GlaxoSmithKline website.
Stamatas, G.N., et al. Lipid uptake and skin occlusion following topical application of oils on adult and infant skin, Journal of Dermatological Science 2008: 50: 135-142.
Arzhavitina, et al. Foams for pharmaceutical and cosmetic application, International Journal of Pharmaceutics 2010 394: 1-17.
Tsutsumi, H., et al. Study on the occiusivity of oil films, J.Soc. Cosmel.Chem. 1979, 30, 345-356.
Quick-FDS [17333-32226-27476-014335]; Jun. 15, 2015-08:57:06; 09 Pages.

\* cited by examiner

TOPICAL COMPOSITIONS COMPRISING A CORTICOSTEROID

RELATED APPLICATIONS

This application is a continuation of U.S. patent application Ser. No. 15/068,428 filed Mar. 11, 2016, which is a continuation-in-part of U.S. patent application Ser. No. 14/645,297 filed Mar. 11, 2015, which claims priority from U.S. Provisional Application Ser. No. 61/951,188 filed Mar. 11, 2014, the entire disclosures of which are incorporated herein by this reference.

TECHNICAL FIELD

The present invention relates to a topical composition comprising a corticosteroid and at least one penetration enhancing agent, wherein the composition is substantially free of propylene glycol.

BACKGROUND

Topical corticosteroids are the most frequently prescribed drugs by dermatologists for treating psoriasis, relief of the inflammatory and pruritic manifestations of steroid responsive dermatoses, and associated diseases or disorders. The corticosteroids are a class of compounds comprising steroids (lipids that contain a hydrogenated cyclopentoperhydrophenanthrene ring system) elaborated by the adrenal cortex (except sex hormones of adrenal origin) in response to the release of adrenocorticotrophin or adrenocorticotropic hormone by the pituitary gland, or to any synthetic equivalent, or to angiotensin II. In pharmacologic doses, corticosteroids are used primarily for their anti-inflammatory and/or immunosuppressive effects.

Topical corticosteroids, such as clobetasol propionate, are effective in treatment of corticosteroid-responsive dermatoses primarily because of their anti-inflammatory, antipruritic and vasoconstrictive actions. Clobetasol propionate is used to treat various other skin disorders including eczema and psoriasis. It is also highly effective for contact dermatitis caused by exposure to poison ivy/oak.

Clobetasol propionate is chemically known as [17-(2'-chloroacetyl)-9-fluoro-11-hydroxy-10,13,16-trimethyl-3-oxo-6,7,8,11,12,14,15,16-octahydrocyclopenta[a]phenanthren-17-yl] propanoate and is represented by structural Formula I:

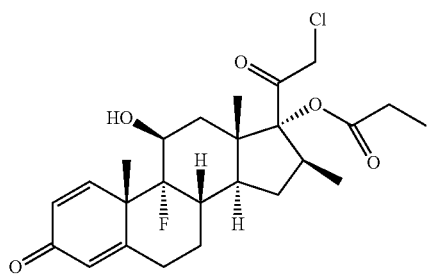

Formula I

Clobetasol propionate is commercially available in compositions for topical application in the form of aerosol foam, cream, ointment, gel, solution, lotion, spray or shampoo, in a weight concentration of 0.05%. TEMOVATE® cream is a commercially available product of clobetasol approved by U.S. Food and Drug Administration (FDA) on Dec. 27, 1985 and is currently being marketed by Fougera Pharms. TEMOVATE® cream contains Clobetasol propionate 0.5 mg/g in a cream base of propylene glycol, glyceryl monostearate, cetostearyl alcohol, glyceryl stearate, PEG 100 stearate, white wax, chlorocresol, sodium citrate, citric acid monohydrate and purified water. TEMOVATE® E is another approved product by U.S. Food and Drug Administration (FDA) containing Clobetasol propionate (0.05% (w/w)) in a cream base of cetostearyl alcohol, isopropyl myristate, propylene glycol, ceteth-20, dimethicone 350, citric acid monohydrate, sodium citrate, imidurea, and purified water.

U.S. Pat. No. 5,972,920 is related to a formulation characterized by a carrier compound formed of a combination of two components in a volume ratio of about 50/50, wherein a first carrier component is selected from the group consisting essentially of ethyl alcohol and isopropyl alcohol and a second carrier component is selected from the group consisting essentially of isopropyl myristate, isopropyl palmitate, octyl palmitate, octyl isononanoate, and isocetyl stearate. The formulation also comprises an anionic surfactant.

PCT Application WO 2006/115987 is related to a method for treating psoriasis by spraying a pharmaceutical composition containing an effective amount of clobetasol propionate onto the skin with psoriasis, using a daily treatment for at least 4 weeks. The preferred composition is a spray formulation of clobetasol propionate 0.05%, containing alcohol, isopropyl myristate, an anionic surfactant such as sodium lauryl sulfate, and optionally, an antimicrobial compound such as an antifungal compound, e.g., undecylenic acid.

U.S. Pat. Nos. 6,419,913 and 6,284,234 are related to topical delivery systems for active agents comprising micellar compositions.

U.S. Publication No. 2006/0099173 is related to a process of making a pharmaceutical composition for topical application, the composition being an emulsion comprising water and at least one active ingredient.

U.S. Publication No. 2007/0142343 is related to a composition comprising corticosteroids, penetration enhancers, solvents and emulsifiers. The vehicle of this composition utilizes at least two penetration enhancers, including diisopropyl adipate, dimethyl isosorbide, propylene glycol, 1,2, 6-hexanetriol, and benzyl alcohol.

US publication No. 2009/0104131 is related to a topically applicable compositions in the form of oil-in-water (O/W) emulsions contain a pro-penetrating system including at least one glycol and at least one additional pro-penetrating agent, a suitable emulsifying system and at least one active agent of the family of steroidal anti-inflammatory agents. Propylene glycol is disclosed as pro-penetrating agent.

U.S. Pat. No. 6,579,512 is related to topical spray composition comprising clobetasol propionate, ethanol, propellant and isopropyl myristate.

U.S. Pat. Nos. 7,700,081 and 7,316,810 are related to clobetasol propionate (0.05 wt %) shampoo compositions used for washing and treating the ailments of scalp.

Dermatological corticosteroids, in particular clobetasol propionate topical preparations face multiple problems, such as delivery efficiency, stability, and tolerability, in particular with respect to excipients that would not cause irritation. In addition, corticosteroids can be absorbed through the skin and can cause systemic side effects, for example hypothalamic pituitary adrenal (HPA) axis suppression. Therefore, to avoid unwanted side effects, the corticosteroid is used at a concentration as low as possible. However, topical preparations containing low concentrations corticosteroids cannot ensure a sufficient therapeutic effect.

U.S. Publication No. 2010/0249060 is related to a low dose clobetasol propionate composition in aqueous vehicle based on propylene glycol and macrogol-glycerol hydroxystearate.

Although several of the above noted references disclose clobetasol propionate containing compositions, most of them are greasy, and hence are unpleasant to apply on large areas of the skin. In addition, some conventional cream and ointment bases containing propylene glycol are irritating to the skin, particularly over the long exposure that is frequently required for efficacy. The fluidity of lotions often makes their physical application difficult to control over a desired area. Further, formulations containing ethanol or propylene glycol may be associated with an elevated risk of sensitization and have a tendency to induce irritation, and thus, such formulations do not promote patient compliance. The currently available topical compositions comprising clobetasol appears to show adverse effect on endocrine system as described in TEMOVATE® cream and TEMOVATE® E cream labels (Hypothalamic-pituitary-adrenal axis suppression).

Accordingly, there is a long felt need to develop effective topical clobetasol composition with reduced concentration of active, but having an effect comparable to that obtainable with conventional topical clobetasol propionate compositions. Further it is desirable to have a clobetasol propionate composition with improved absorption without causing any skin irritation.

SUMMARY OF THE INVENTION

Accordingly, provided herein, in some embodiments, is a topical pharmaceutical composition including at least one corticosteroid and at least one penetration enhancing agent.

In some embodiments, a topical pharmaceutical composition includes between 0.015% and 0.035% (w/w) clobetasol; at least one alcohol selected from the group-consisting of fatty alcohols, PEGylated fatty alcohols, long chain alcohols, isopropyl alcohol, benzyl alcohol, branched aliphatic alcohols, lanolin alcohol, polyvinyl alcohols, and combinations thereof a penetration enhancing agent; an emulsifying agent; an aqueous phase; and an oil phase. In one embodiment, the clobetasol is clobetasol propionate. In one embodiment, the penetration enhancing agent is selected from group consisting of polyols, glycols (except propylene glycol), ethers, glycol ethers, esters, sulfoxides, fatty acids, fatty acid esters, essential oils, terpenes, terpenoids, PEGylated fatty acids, PEGylated fatty acid esters and mixtures thereof nitrogenous compounds, alkanones, organic acids, and combinations thereof. In another embodiment, the penetration enhancing agent is diethylene glycol monoethyl ether.

In some embodiments, the composition is an oil-in-water emulsion. In some embodiments, the composition has a viscosity of from about 0.1 cP to about 500 cP when measured by Brookfield viscometer Cap 2000+ with spindle no. 1 at 530 rpm at 25° C. In some embodiments, the composition is substantially free of propylene glycol. In some embodiments, the composition further includes at least one non-polymeric thickening agent. In one embodiment, the non-polymeric thickening agent is selected from the group consisting of cetyl alcohol, paraffin, stearyl alcohol, white wax, wax cetyl esters, microcrystalline wax, anionic emulsifying wax, non-ionic emulsifying wax, yellow wax, castor oil, ceresin, cetostearyl alcohol, cyclomethicone, glyceryl behenate, hectorite, myristyl alcohol, cetylstearyl alcohol, triolein, lanolin, and combinations thereof. In some embodiments, the aqueous phase includes water. In some embodiments, the oil phase includes the penetration enhancing agent.

Also provided herein, in some embodiments, is a method of treating a skin disease or disorder, the method including topically administering a topical composition comprising between 0.015% and 0.035% (w/w) clobetasol; at least one alcohol selected from the group-consisting of fatty alcohols, PEGylated fatty alcohols, long chain alcohols, isopropyl alcohol, benzyl alcohol, branched aliphatic alcohols, lanolin alcohol, polyvinyl alcohols, and combinations thereof; a penetration enhancing agent; an emulsifying agent; an aqueous phase; and an oil phase to an individual in need of treatment.

DETAILED DESCRIPTION OF THE INVENTION

Figure 1:
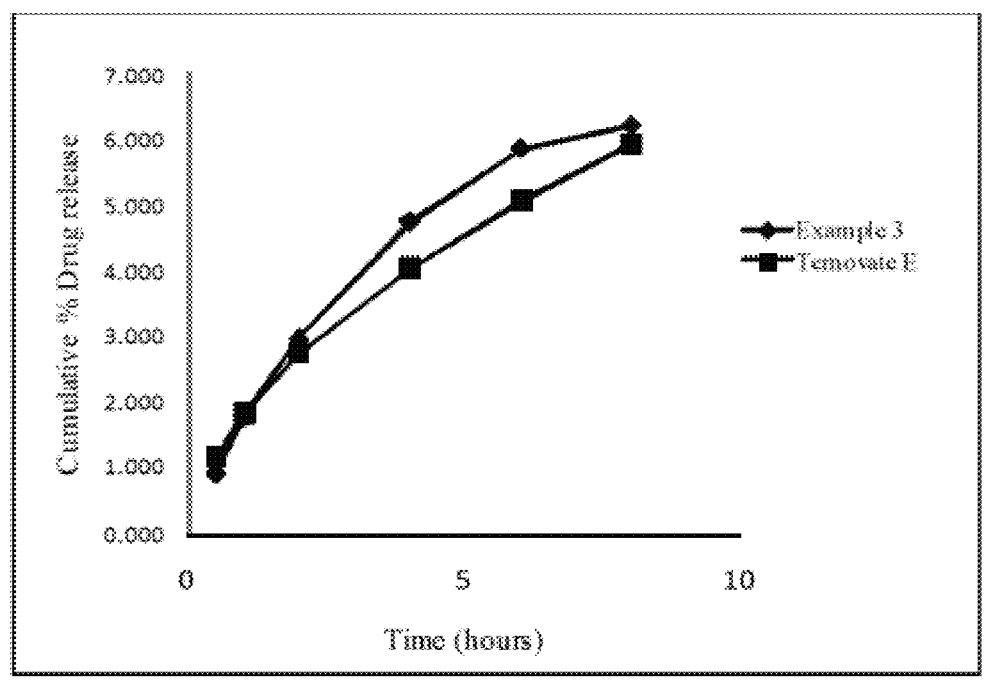
FIG. 1 shows drug release for a composition of the invention and a commercially available product.

The details of one or more embodiments of the present invention are set forth in this document. Modifications to embodiments described in this document, and other embodiments, will be evident to those of ordinary skill in the art after a study of the information provided in this document. The information provided in this document, and particularly the specific details of the described exemplary embodiments, is provided primarily for clearness of understanding and no unnecessary limitations are to be understood therefrom. In case of conflict, the specification of this document, including definitions, will control.

Definitions: The terms as used herein have the following meanings:

Clobetasol, as used herein, encompasses pharmaceutically acceptable, pharmacologically active derivatives of clobetasol, including clobetasol propionate, clobetasol base form, its ester form, its isomer form, both individual enantiomers of clobetasol (dextrogyral and levogyral enantiomers) in their substantially pure form and their pharmaceutically acceptable salts, mixtures (in any ratio) of clobetasol enantiomers and their pharmaceutically acceptable salts, and active metabolites of clobetasol and their pharmaceutically acceptable salts, unless otherwise noted. The solid state form of clobetasol used in the composition of the present invention is not critical. For example, clobetasol propionate can be amorphous or crystalline. As will be recognized by one of ordinary skill in the art upon study of this application, clobetasol(s) are corticosteroids. In some embodiment, the terms "active", "active agent", or "compound" herein refers to corticosteroids, including clobetasol, or to pharmaceutically acceptable forms thereof.

The term "low-dose clobetasol" means clobetasol is present in an amount from about 0.005% to about 0.045% (w/w). In some embodiments, low-dose clobetasol is provided from about 0.005% to about 0.045% (w/w). In some embodiments, low-dose clobetasol is provided at a dose of about 0.005%, 0.01%, 0.015%, 0.02%, or 0.025% to about 0.03%, 0.035%, or 0.04% (w/w). In some embodiments, low-dose clobetasol is provided at a dose of about 0.005%, 0.01%, 0.015%, 0.02%, or 0.025% to about 0.03%, 0.035%, or 0.04% (w/w) 0.045% (w/w).

The term "substantially free" as used herein indicates that the specified substance referred to is present in amounts not more than 10% by weight of the total composition or in amounts not more than about 9% by weight of the total composition, or in amounts not more than about 8% by weight of the total composition, or in amounts not more than about 7% by weight of the total composition, or in amounts not more than about 6% by weight of the total composition, or in amounts not more than about 5% by weight of the total composition, or in amounts not more than about 4% by weight of the total composition, or in amounts not more than about 3% by weight of the total composition, or in amounts not more than about 2% by weight of the total composition or in amounts not more than about 1% by weight of the total composition or in an amount about 0% by weight of the total composition or completely free of specified substance i.e. 0%.

The term "pharmaceutically-acceptable" as used herein, means that inert excipients are suitable for use in contact with the tissues of humans and lower animals without undue toxicity, incompatibility, instability, irritation, allergic response, and the like, commensurate with a reasonable benefit/risk ratio.

The term "substantially free of adverse effects" as used herein means at least about 90% of total patient population does not have adverse effects resultant from clobetasol based compositions or about 80% of total patient population does not adverse effects or at least about 70% of total patient population does not have adverse effects or at least about 60% of total patient population does not have adverse effects. For example, about 90% of total patient population does not have HPA axis suppression or about 80% of total patient population does not have HPA axis suppression or at least about 70% of total patient population does not have HPA axis suppression or at least about 60% of total patient population does not have HPA axis suppression. In some embodiments, "substantially free of HPA axis suppression" as used herein means at least about 90% of total patient population does not have HPA axis suppression or about 80% of total patient population does not HPA axis suppression or at least about 70% of total patient population does not have HPA axis suppression or at least about 60% of total patient population does not have HPA axis suppression. Another adverse effect is reduction in the serum concentration of DHEAS and the percentage reduction of serum concentration of DHEAS is less than about 18% or the percentage reduction of serum concentration of DHEAS is less than about 15%, the percentage reduction of serum concentration of DHEAS is less than about 12%.

The term "adverse effect" as used herein means adverse effects of the high-mid potent topical steroids such as clobetasol, and the adverse effects are significant effect on endocrine system. Adverse effects as defined in this application encompasses reversible suppression of the hypothalamic-pituitary-adrenal (HPA) axis and/or the reduction in the serum levels of dehydroepiandrosterone (DHEA) and/or dehydroepiandrosterone sulfate (DHEAS).

"Clinically significant" means a change that will produce an adverse physiological effect.

The term "highest approved topical dose of clobetasol" as used herein refers to a highest approved topical dose of clobetasol propionate by US Food and drug administration (US FDA) for the treatment of one or more of skin disorders and the highest approved topical dose of clobetasol propionate by US FDA is 0.05% (w/w), i.e. TEMOVATE® or TEMOVATE® E. The term "TEMOVATE®" is used interchangeably for indicating "highest approved topical dose of clobetasol propionate' i.e. 0.05% (w/w) in cream or gel or ointment or solution form; or its pharmaceutical equivalents or its therapeutic equivalents or later approved drugs which are designated as AB rated by US FDA as per *Approved Drug Products with Therapeutic Equivalence Evaluations* ($34^{th}$ *edition*) or drugs obtained marketing approval by US FDA through Abbreviated New Drug Application (ANDA) filing by establishing bioequivalence to such Product". For example, TEMOVATE® Cream comprises clobetasol propionate 0.5 mg/g in a cream base of propylene glycol, glyceryl monostearate, cetostearyl alcohol, glyceryl stearate, PEG 100 stearate, white wax, chlorocresol, sodium citrate, citric acid monohydrate, and purified water. TEMOVATE® Ointment comprises clobetasol propionate 0.5 mg/g in a base of propylene glycol, sorbitan sesquioleate, and white petrolatum. Excipient details of other compositions such Therapeutic equivalents/Pharmaceutical equivalents of TEMOVATE® gel or TEMOVATE® gel or TEMOVATE® solution can be found from US FDA or any other public literature. In some embodiments TEMOVATE® includes its US FDA therapeutic or pharmaceutical equivalents. In some embodiments TEMOVATE® cream includes its US FDA therapeutic or pharmaceutical equivalents. TEMOVATE® is a Trademark originally registered by Glaxo Group Limited Corporation Great Britain Clarges house, 6-12 Clarges Street London England W1Y8DH. Last listed owner of this Trademark is Fougera Pharmaceuticals, inc. Corporation New York 60 Baylis Road Melville N.Y. 11747.

The term "plasma concentrations of clobetasol" as used herein indicates that plasma concentrations of clobetasol base or its pharmaceutically acceptable salts or degradants, unless until specific salt form is denoted; or in some embodiments "plasma concentrations of clobetasol" indicates plasma concentrations of clobetasol propionate or clobetasol base.

The term "post treatment" as used herein to refer to the time period post to the topical treatment course of about 2 weeks or 15 days.

The term "clobetasol plasma levels insufficient to reduce serum levels cortisol less than or equal to 18 ug/dL" is used herein to indicate any plasma concentration of clobetasol which does not provide HPA axis suppression to the subject treated with topical composition of the present invention, and such plasma concentrations may be selected from about 1000 pg/ml to about 10 pg/ml or below quantifiable limit (<=10 pg/ml).

Terms such as "about," "up to", "generally", "substantially" and the like are to be construed as modifying a term or value such that it is not an absolute. Such terms will be defined by the circumstances and the terms that they modify as those terms are understood by those of skill in the art. This includes, at very least, the degree of expected experimental error, technical error and instrumental error for a given experiment, technique or an instrument used to measure a value.

Unless otherwise indicated, all numbers expressing quantities of ingredients, properties such as reaction conditions, and so forth used in the specification and claims are to be understood as being modified in all instances by the term "about". Accordingly, unless indicated to the contrary, the numerical parameters set forth in this specification and claims are approximations that can vary depending upon the desired properties sought to be obtained by the present invention.

As used herein, ranges can be expressed as from "about" one particular value, and/or to "about" another particular value. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

The present invention can comprise or consist essentially of the components of the present invention as well as other ingredients or elements described herein. As used herein, "comprising" means the elements recited, or their equivalent in structure or function, plus any other element or elements which are not recited. The terms "having," "including," and "comprised of" are also to be construed as open ended unless the context suggests otherwise. As used herein, "consisting essentially of" means that the invention may include ingredients in addition to those recited in the claim, but only if the additional ingredients do not materially alter the basic and novel characteristics of the claimed invention.

As used herein, "optional" or "optionally" means that the subsequently described event or circumstance does or does not occur or exist and that the description includes instances where said event or circumstance occurs or exists, and instances where it does not.

The term "improved efficacy" or "improving efficacy" or "improving therapeutic efficacy" as used herein refers to the therapeutically beneficial effects of the topical active with reduction of systemic adverse effects as described in the present invention.

The term "therapeutic efficacy" as used herein means converting a subject with "very severe or severe" or "moderate conditions" to "mild" or "minimal or almost clear" or "clear" lesions in the scheduled treatment period and this clinical determinations using Investigator Global Assessment (IGA) scoring method or by vasocontrictor assay (VCA) method (skin blanching assay) for corticosteroids or any suitable method of accessing corticosteroids activity in skin. In some embodiments, the term subject refers to a patient suffering from skin disorders such as psoriasis. In some embodiments, the term "subject" refers to a patient involving psoriasis of at least about 5% body surface area or a patient involving psoriasis of at least about 10% body surface area or a patient involving psoriasis of more than about 10% body surface area.

The term "enhanced flux" as used herein refers to increase in the skin permeation of the active in skin layers of the subject up to dermis with less systemic exposure. i.e., enhanced flux allows to utilize lower dose of active to treat disease condition effectively.

The term "penetration enhancing agent(s)" as used herein means compounds that enhance the penetration rate of a corticosteroid through the skin or mucous membrane, such as by temporarily diminishing the impermeability of the skin or mucous membrane.

Generally, a penetration enhancing agent is a component used to enhance the penetration rate of steroid through the skin or mucous membrane, such as by temporarily diminishing the impermeability of the skin or membrane. Penetration enhancing agents are also been known as "accelerants" and "absorption promoters."

Examples of suitable penetration enhancing agents include, but are not limited to, polyols, glycols (except propylene glycol), ethers, glycol ethers, esters, sulfoxides, fatty acids, fatty acid esters, fatty alcohols, essential oils, terpenes, terpenoids, PEGylated fatty acids, PEGylated fatty acid esters, PEGylated fatty alcohols and mixtures thereof, including polyethylene glycol, polyethylene glycol monolaurate, and butanediol; sulfoxides, including dimethylsulfoxide and decylmethylsulfoxide; ethers, including diethylene glycol monoethyl ether and diethylene glycol monomethyl ether; fatty acids, including lauric acid, oleic acid, and valeric acid; fatty acid esters, including isopropyl myristate, isopropyl palmitate, methyl propionate, and ethyl oleate; nitrogenous compounds including urea, dimethyl acetamide, dimethylformamide 2-pyrrolidone, ethanolamine, methyl-2-pyrrolidone, diethanolamine, and triethanolamine; terpenes; terpenoids; alkanones; organic acids, including salicylic acid, citric acid, and succinic acid; and combinations comprising one or more of the foregoing materials. In some embodiments, the penetration enhancing agent used in the pharmaceutical composition of the present invention is diethylene glycol monoethyl ether. In some embodiments, the penetration enhancing agent is not polypropylene glycol. The penetration enhancing agent(s) may interchangeably be used as solvent.

The term "localized region," as used herein refers to a discrete location on the body surface of the subject, such as a location experiencing a symptom of condition being treated. As used herein, the term "subject" includes both human and animal subjects. Thus, veterinary therapeutic uses, as well as uses in connection with human subjects, are provided in accordance with the present invention.

As used herein, the terms "treatment" or "treating" relate to curing or substantially curing a condition, as well as ameliorating at least one symptom of the condition, and are inclusive of prophylactic treatment and therapeutic treatment. As would be recognized by one or ordinary skill in the art, treatment that is administered prior to clinical manifestation of a condition then the treatment is prophylactic (i.e., it protects the subject against developing the condition). If the treatment is administered after manifestation of the condition, the treatment is therapeutic (i.e., it is intended to diminish, ameliorate, control, or maintain the existing condition and/or side effects associated with the condition). The terms relate to medical management of a subject with the intent to substantially cure, ameliorate, stabilize, or substantially prevent a condition, including but not limited to prophylactic treatment to preclude, avert, obviate, forestall, stop, or hinder something from happening, or reduce the severity of something happening, especially by advance action. As such, the terms treatment or treating include, but are not limited to: inhibiting the progression of a condition of interest; arresting or preventing the development of a condition of interest; reducing the severity of a condition of interest; ameliorating or relieving symptoms associated with a condition of interest; causing a regression of the condition of interest or one or more of the symptoms associated with the condition of interest; and preventing a condition of interest or the development of a condition of interest.

The present invention includes a topical composition including a corticosteroid. In some embodiments, the present invention provides a topical pharmaceutical composition comprising at least one corticosteroid and at least one penetration enhancing agent. The composition of the present invention is substantially free of propylene glycol. In some embodiments, the composition includes not more than 10, 9, 8, 7, 6, 5, 4, 3, 2, or 1% by weight of the total composition.

Thus, in some embodiments, the composition is substantially free of polypropylene glycol where there is less than 1% by weight polypropylene glycol in the total composition. In other embodiments, the composition is substantially free of polypropylene glycol where there is less than 2, 3, 4, 5, 6, 7, 8, 9, or 10% by weight polypropylene glycol in the total composition. In other embodiments, the composition is substantially free of polypropylene glycol where there is less than about 0% by weight polypropylene in the total composition.

In some embodiments, the present invention provides a topical pharmaceutical composition comprising therapeutically effective amount of clobetasol propionate, at least one penetration enhancing agent and at least one pharmaceutically acceptable excipient, wherein the composition is substantially free of propylene glycol. In some embodiments, the present invention provides a method to provide an enhanced flux of clobetasol propionate through the localized region of the body surface to reach the dermis layer, comprising administering to an individual the effective amount of topical pharmaceutical composition comprising: (a) low dose of clobetasol propionate, (b) an oil phase comprising: at least one penetration enhancing agent and a non-polymeric thickening agent, (c) an aqueous phase; and (d) optionally, at least one pharmaceutically acceptable excipient; wherein the composition is substantially free of propylene glycol and substantially free of polymers.

In some embodiments, the composition of the present application provides comparable or enhanced efficacy over the commercially available clobetasol propionate 0.05% (w/w) cream composition (TEMOVATE E® cream) and does not show significant adverse effect on endocrine system as described herein and as known to those of ordinary skill in the art.

Topical corticosteroids provide adverse effect on human endocrine system. High potent corticosteroids show high incidence of systemic side effects such as suppression of hypothalamus-pituitary-adrenal (HPA) axis this effect is reversible. Topical corticosteroids are absorbed systematically and show suppression of HPA axis. The HPA axis suppression is critical safety issue in topical corticosteroid therapy. The HPA axis suppression is generally evaluated by certain parameters such as levels of cortisol and levels of dehydroepiandrosterone (DHEA) and dehydroepiandrosterone sulfate (DHEAS) in a subject's blood during treatment schedule. The cortisol levels are determined by ACTH (cosyntropin) stimulation test. The ACTH stimulation test measures how the adrenal glands respond to adrenocorticotropic hormone (ACTH). ACTH is a hormone produced in the pituitary gland that stimulates the adrenal glands to release a hormone called cortisol. The man-made form of ACTH is called cosyntropin. The normal level of cortisol is less than 18 mcg/dL in a normal subject and cortisol level goes higher than 18 to 20 micrograms per deciliter (mcg/dL) after ACTH injection to the subject and similarly DHEA/DHEAS levels also changes in a subject who undergo treatment with topical corticosteroids, generally the standard reference range of DHEA is 280-640 µg/dL in men and 65-380 µg/dL is in women.

Clobetasol propionate is a highly potent topical corticosteroid, which is known to have effect on endocrine system which suppresses the HPA axis at doses as low as 2 grams per day. Shortcomings of the previously-described therapy include necessity of periodic evaluation for HPA axis suppression and modification in dosing and administrating schedule due to the HPA axis suppression.

Distinctly, the topical composition of the present invention does not show significant adverse effect on endocrine system, when applied twice daily for 15 days (2 weeks) in the subjects having affected body surface area of at least 20% up to 50% excluding face, scalp, groin, axillae and other intertriginous areas.

In some embodiments, the topical composition of the present invention comprises a therapeutically effective amount of clobetasol; an oil phase comprising at least one skin penetration enhancer; an aqueous phase and optionally one pharmaceutically acceptable excipient.

In some embodiments, the present invention provides a method for prophylaxis, amelioration, or treatment of psoriasis, relief of the inflammatory and pruritic manifestations of steroid responsive dermatoses, erythema, contact sensitivity reactions, and other associated diseases or disorders, by administering to an individual the effective amount of topical composition comprising:
(a) a low dose of clobetasol propionate,
(b) an oil phase comprising: at least one penetration enhancing agent and a non-polymeric thickening agent,
(c) an aqueous phase; and
(d) optionally, at least one pharmaceutically acceptable excipient; wherein the composition is substantially free of propylene glycol and substantially free of polymers.

In some embodiments, the clobetasol present in the composition amounts from about 0.005% to about 0.1% of the total weight of the composition. In some embodiments, the clobetasol propionate is present in amounts from about 0.005% to about 0.05% of the composition, or in amounts up to about 0.025% of the total weight of the composition.

In some embodiments of the present invention, the clobetasol propionate is present in amounts up to about 0.005, 0.006, 0.007, 0.008, 0.009, 0.010, 0.011, 0.012, 0.013, 0.014, 0.015, 0.016, 0.017, 0.018, 0.019, 0.020, 0.021, 0.022, 0.023, 0.024, 0.025, 0.026, 0.027, 0.028, 0.029, 0.030, 0.031, 0.032, 0.033, 0.034, 0.035, 0.036, 0.037, 0.038, 0.039, 0.040, 0.041, 0.042, 0.043, 0.044, or 0.045% of the total weight of the composition. In some embodiments, the clobetasol propionate is present in amounts of less than 0.050% of the total weight of the composition. In some embodiments, the clobetasol propionate is present in amounts of about 0.010 to about 0.040% of the total weight of the composition. In some embodiments, the clobetasol propionate is present in amounts of about 0.015 to about 0.035% of the total weight of the composition. In some embodiments, the clobetasol propionate is present in amounts of about 0.020 to about 0.030% of the total weight of the composition.

In other embodiments, the composition of the present invention comprises at least one penetration enhancing agent in an amount of from about 1% to about 30.0% of the weight of the composition, or in amounts of from about 0.01% to about 10.0% of the composition. In some embodiments of the present invention, the at least one penetration enhancing agent is provided in amounts up to about 0.05, 0.10, 0.15, 0.20, 0.25, 0.30, 0.35, 0.40, 0.45, 0.50, 0.55, 0.60, 0.65, 0.70, 0.75, 0.80, 0.85, 0.90, 0.95, 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, or 10% of the weight of the composition.

In another embodiment, the present invention provides a topical pharmaceutical composition comprising: a low dose of clobetasol propionate in an amount selected from about 0.005% to about 0.1% of the total weight of the composition; an oil phase comprising at least one penetration enhancing agent in an amount from about 0.01% to about 15.0% of the total weight of the composition and a non-polymeric thickening agent, an aqueous phase, and optionally, at least one pharmaceutically acceptable excipient, wherein the composition is substantially free of propylene glycol and substantially free of polymers.

In yet another embodiment, the present invention provides a method for prophylaxis, amelioration or treatment of skin diseases or disorders such as psoriasis/psoriatic plaques, relief of the inflammatory and pruritic manifestations of steroid responsive dermatoses, erythema, contact sensitivity reactions, atopic dermatitis, seborrhoeic dermatitis, eczema, plaque psoriasis, erythrodermic psoriasis, psoriasis of the scalp, and other associated diseases or disorders, by administering to an individual an effective amount of a topical composition comprising: (a) clobetasol propionate in an amount of about 0.025% of the total weight of the composition, (b) an oil phase comprising: at least one penetration enhancing agent and a non-polymeric thickening agent, (c) an aqueous phase, and (d) at least one pharmaceutically acceptable excipient, wherein the composition is substantially free of propylene glycol and the composition has comparable or improved efficacy compared to the commercially available clobetasol propionate 0.05% (w/w) cream composition (TEMOVATE® cream). In some embodiments, the topical composition is administered twice-a-day for a period of 4 weeks or topical composition is administered twice-a-day for a period of at least 2 weeks.

In another embodiment, the penetration enhancing agent used in the present invention is selected from the group consisting of polyols, glycols (except propylene glycol), ethers, glycol ethers, esters, sulfoxides, fatty acids, fatty acid esters, fatty alcohols, essential oils, terpenes, terpenoids, PEGylated fatty acids, PEGylated fatty acid esters, PEGylated fatty alcohols, and mixtures thereof.

In other embodiments of the present invention, the penetration enhancing agent is diethylene glycol monoethylether.

In some embodiments, a composition of the present invention comprises one or more additional active agents that are useful in the management of psoriasis and associated pathological conditions including synthetic, semi-synthetic, or naturally obtained active agents.

The composition of the present invention can be used for prophylaxis, amelioration, or treatment of skin diseases and disorders, by administering a pharmaceutically effective amount of the composition to a subject in need thereof. The compositions of the present invention are also useful in conjunction with other therapies, such as phototherapy.

In other embodiments, the present invention provides a process for preparing a topical pharmaceutical composition, comprising:

(i) preparing an oil phase by melting and stirring thickening agent(s), emulsifier(s) followed by preservative(s) and emollient(s);

(ii) preparing an aqueous phase by heating water, (iii) preparing an emulsion by adding the oil phase of step (i) to the aqueous phase of step (ii) or vice versa under constant homogenization, (iv) dissolving a premixed solution of clobetasol in a solvent followed by addition of an antioxidant(s) and homogenizing to obtain a clobetasol solution, and (v) adding the clobetasol solution obtained in step (iv) to the emulsion prepared in step (iii) followed by homogenization and cooling to obtain a cream composition.

In still further embodiments, the present invention provides a process for preparing topical pharmaceutical composition comprising:

(i) preparing an oil phase by melting and stirring stearyl alcohol, cetyl alcohol, whitewax; glyceryl stearate and PEG 100 stearate and emollient, followed by methyl paraben and propyl paraben, and the remaining part of the mineral oil, (ii) preparing an aqueous phase by adding sorbitol solution into heated water, (iii) preparing an emulsion by adding the oil phase of step (i) to the aqueous phase (ii) or vice versa under homogenization, dissolving a premixed solution of clobetasol propionate in a diethylene glycol monoethyl ether and the followed by addition of BHT and homogenizing to obtain a clobetasol propionate solution, and (iv) adding the steroid solution obtained in step (iv) to the emulsion prepared in step (iii) followed by homogenization to obtain a cream composition.

In further embodiments, the compositions of the present invention using one or more other corticosteroids can be prepared by using a process similar to that described above.

The topical pharmaceutical composition of the present invention is useful in the prophylaxis, amelioration or treatment of skin diseases or disorders such as psoriasis/psoriatic plaques, relief of the inflammatory and pruritic manifestations of steroid responsive dermatoses, erythema, contact sensitivity reactions, atopic dermatitis, seborrhoeic dermatitis, eczema, plaque psoriasis, erythrodermic psoriasis, psoriasis of the scalp, and other associated diseases or disorders.

In some embodiments of the present invention, it was surprisingly found that the topical compositions of the invention containing an oil phase that comprises at least one penetration enhancing agent, and an aqueous phase, provides an enhanced flux of clobetasol through the localized region of the body surface to reach the dermis layer; this advantageously allows for the use of a lower concentration of clobetasol, i.e., about 50% less than the commercially available dosage form TEMOVATE® cream (which contains 0.05% (w/w) of clobetasol propionate), while providing a similar or improved efficacy and provides no significant effect on endocrine system i.e., HPA axis suppression.

In still further embodiments of the invention, it has now been found that the pharmaceutical composition of the present invention containing 3% of penetration enhancing agent provides similar or improved efficacy as compared to TEMOVATE® cream (which contains 0.05% (w/w) of clobetasol propionate). In further embodiments of the invention, the pharmaceutical composition of the present invention containing 10% of penetration enhancing agent.

Further, it is observed that the topical pharmaceutical composition of the present invention, which is free of propylene glycol, is non-irritating, non-toxic, and well-tolerated and are free of any undesired attributes, thereby providing a high degree of patient compliance.

In other embodiments, compositions of the present application present invention are physically and chemically stable.

In other embodiments, topical pharmaceutical compositions of the present invention are useful in the relief of the inflammatory and pruritic manifestations of steroid responsive dermatoses, and further can provide a moisturizing and/or soothing effect at the site of application to the skin. The composition of the application reduces the dryness that accompanies the build-up of skin in psoriatic plaques.

In other embodiments, the composition of the application can be applied directly to the psoriatic lesions or dermatoses and can help reduce inflammation, remove built-up scale, reduce skin turnover, and/or clear affected skin of plaques.

In some embodiment, the compositions of the present invention can utilize any topical corticosteroids, either alone or in combination of others. Suitable examples of topical corticosteroids include, but not limited to, clobetasol propionate, alclometasone dipropionate, amcinonide, beclomethasone dipropionate, betamethasone benzoate, betamethasone dipropionate, betamethasone sodium phosphate, betamethasone valerate, budesonide, clocortolone pivalate, desonide, desoximetasone, dexamethasone, dexamethasone acetate, dexamethasone nicotinate, dexamethasone propionate, dexamethasone sodium phosphate, dexamethasone valerate, diflorasone diacetate, diflucortolone valerate, flurandrenolide, flumethasone pivalate, fluocinolone acetonide, fluocinonide, fluocortin butyl ester, fluticasone propionate, halcinonide, halobetasol propionate, halometasone monohydrate, hydrocortisone, hydrocortisone sodium phosphate, hydrocortisone sodium succinate, hydrocortisone-17-butyrate-21-propionate, hydrocortisone aceponate, hydrocortisone acetate, hydrocortisone valerate, hydrocortisone butyrate, hydrocortisone probutate, methylprednisolone, methylprednisolone acetate, methylprednisolone aceponate, mometasone furoate, prednisolone, prednisolone sodium phosphate, prednisolone acetate, prednisolone-17-valerate-21-acetate, triamcinolone acetonide, triamcinolone acetate, triamcinolone diacetate, and prednicarbate. Other drug compounds are also useful, and this application further specifically contemplates the use of any combinations of steroid drugs.

The topical compositions of the present invention may be in the form of solution, suspension, emulsions, creams, ointments, lotions, microemulsions, nanoemulsions, emulgels, liposomes, micelle, reverse micelle, gels, hydrogels, sprays and the like.

In an embodiment, the topical composition of the present invention may be in form of compositions, comprising two phases: an oil phase and an aqueous phase and compositions of the present invention may be in the form of emulsions, creams, lotions, microemulsions, nanoemulsions, emulgels, liposomes, micelles, reverse micelle, spray and the like. In some embodiments, compositions may be in the form of an emulsion. The emulsion can be in the form of an oil-in-water type of emulsion or a water-in-oil type of emulsion. An aqueous-based emulsion, such as an oil-in-water emulsion, frequently has lower viscosity than other emulsion types and exhibits appreciable storage stability and patient compliance. Generally, oil-in-water emulsions have better skin feel properties, when applied to the skin, as these give sensations similar to an aqueous material.

In some embodiments, pharmaceutical compositions of the present invention are formulated as emulsions, comprising an oily or hydrophobic phase, an aqueous or hydrophilic phase, and an emulsifier. When the oily phase is dispersed as droplets within an aqueous continuous phase, this is called an "oil-in-water" type of emulsion. When the aqueous phase is dispersed as droplets within an oily continuous phase, this is called a "water-in-oil" type of emulsion.

In some embodiments, a pharmaceutical composition of the present invention is aqueous-based topical oil-in-water emulsion. The "aqueous-based" term is defined as an emulsion which comprises high percentage of water. The aqueous-based oil-in-water emulsion composition of the present invention comprises at least 60% of water in the final composition, or comprises at least 70% of water in the final composition.

In some embodiments, an aqueous-based topical oil-in-water emulsion composition of the present invention comprises: a therapeutically effective amount of a corticosteroid and at least one pharmaceutically acceptable excipient, wherein the composition is substantially free of propylene glycol and substantially free of polymers.

In some embodiments, an aqueous-based topical oil-in-water emulsion composition of the present invention comprises: (a) a therapeutically acceptable amount of clobetasol (b) a discontinuous oil phase comprising: a solvent and at least one penetration enhancing agent; (c) a continuous aqueous phase; and (d) at least one pharmaceutically acceptable excipient, wherein the composition is substantially free of propylene glycol and substantially free of polymers. In some embodiments, the topical composition comprises: (a) a therapeutically acceptable amount of clobetasol of about 0.025% (w/w); (b) an oil phase comprising: at least one penetration enhancing agent, and a non-polymeric thickening agent; (c) an aqueous phase; and (d) optionally one pharmaceutically acceptable excipient; wherein the said topical composition is substantially free of propylene glycol and substantially free of polymers; wherein the topical composition provides no significant adverse effect on endocrine system.

In further embodiments, an aqueous based topical oil-in-water emulsion composition of the present invention has viscosity in the range of from about 10 cP to about 100000 cP. The viscosities of the aqueous-based emulsion compositions of the present invention may be in the range of about 0.01-100 Pascal second, "Pa·s" (10-1,00,000 cP), or about 0.1 to 100 Pa·s (100-1,00,000 cP) or about 1-50 Pa·s (1000-50,000 cP), or about 0.01-15 Pa·s (10-15,000 centipoise, "cP"), or about 0.02-1.5 Pa·s (20-1,500 cP), or about 0.05-1 Pa·s (50-1,000 cP).

The viscosity of topical compositions of the present invention is in the range of from about 0.1 cP to about 500 cP when measured by Brookfield viscometer Cap 2000+ with spindle no. 1 at 530 rpm at 25° C.

In another embodiment, pharmaceutical composition of the present invention includes one or more pharmaceutically acceptable excipient, which may act as carrier(s), emulsifier(s), co-emulsifier(s) solvent(s), co-solvents(s), emollient(s), antioxidant(s), preservative(s), gelling or thickening agent(s), polymer(s), surfactant(s), soothing agent(s), pH modifier(s), solubilizer(s), humectants(s), moisturizer(s), oily base(s), and the like.

The term 'carrier' or "vehicle" denotes organic or inorganic ingredients, natural or synthetic, with which an active ingredient is combined to facilitate application of a composition. Examples of carriers include, but not limited to, water, acetone, alone or in combination with materials such as silicone fluids. In certain embodiments, the carrier can comprise, in addition to water, water-immiscible substances such as any pharmaceutically acceptable fatty esters of natural fatty acids, triglycerides of animal or vegetable, medium chain triglycerides, mixtures of mono-, di- and/or triglycerides, waxes, hydrogenated vegetable oils, and mixtures thereof.

Examples of emulsifying agents include, but not limited to, disodium cocoampho diacetate, oxyethylenated glyceryl cocoate (7 EO), PEG-20 hexadecenyl succinate, PEG-15 stearyl ether, ricinoleic monoethanolamide monosulfosuccinate salts, oxyethylenated hydrogenated ricinoleic triglyceride containing 60 ethylene oxide units such as the products marketed by BASF under the trademarks CREMOPHOR® RH 60 or CREMOPHOr® RH 40 (polyoxyl 40 hydrogenated castor oil), polymers such as poloxamers, which are block copolymers of ethylene oxide and propylene oxide, and the nonsolid fatty substances at room temperature (that is to say, at temperatures ranging from about 20 to 35° C.) such as sesame oil, sweet almond oil, apricot stone oil, sunflower oil, octoxyglyceryl palmitate (or 2-ethylhexyl glyceryl ether palmitate), octoxyglyceryl behenate (or 2-ethylhexyl glyceryl ether behenate), dioctyl adipate, and tartrates of branched dialcohols. Sorbitan fatty acid esters are a series of mixtures of partial esters of sorbitol and its mono- and dianhydrides with fatty acids. Sorbitan esters include products marketed as ARLACEL® 20, ARLACEL 40, ARLACEL 60, ARLACEL 80, ARLACEL 83, ARLACEL 85, ARLACEL 987, ARLACEL C, PEG-6 stearate and glycol stearate and PEG-32 stearate (TEFOSE® 63), and PEG-6 stearate and PEG-32 stearate (TEFOSE® 1500), glyceryl stearate and PEG 100 stearate (TEFOSE® 165) and any mixtures thereof. Polyethylene glycol ethers of stearic acid are in another group of emulsifiers that can be used in the emulsions. Examples of polyethylene glycol ethers of stearic acid include, but not limited to, steareth-2, steareth-4, steareth-6, steareth-7, steareth-10, steareth-11, steareth-13, steareth-15, steareth-20, polyethylene glycol ethers of stearyl alcohol (steareth 21), and any mixtures thereof. Other emulsifying agents include sodium lauryl sulphate, cetyl trialkyl ammonium bromide, polyoxyethylene sorbitan fatty acid esters, and any mixtures thereof Nonionic emulsifying agents include those that can be broadly defined as condensation products of long chain alcohols, e.g., $C_{8-30}$ alcohols, with sugar or starch polymers, i.e., glycosides. Various sugars include, but not limited to, glucose, fructose, mannose, and galactose, and various long chain alcohols include, but are not limited to, decyl alcohol, cetyl alcohol, stearyl alcohol, lauryl alcohol, myristyl alcohol, oleyl alcohol, and any mixtures thereof.

Other useful nonionic emulsifying agents include condensation products of alkylene oxides with fatty acids such as alkylene oxide esters of fatty acids. Other nonionic surfactants are the condensation products of alkylene oxides with 2 moles of fatty acids such as alkylene oxide diesters of fatty acids.

Emulsifying agents can also include any of a wide variety of cationic, anionic, zwitterionic, and amphoteric surfactants that are known in the art. Examples of anionic emulsifying agents include, but not limited to, alkyl isethionates, alkyl and alkyl ether sulfates and salts thereof, alkyl and alkenyl ether phosphates and salts thereof, alkyl methyl taurates, and soaps (e.g., alkali metal salts and sodium or potassium salts) of fatty acids.

Examples of amphoteric and zwitterionic emulsifying agents include those which are broadly described as derivatives of aliphatic secondary and tertiary amines in which the aliphatic radical can be straight or branched chain, wherein one of the aliphatic substituents contains from about 8 to about 22 carbon atoms and one contains an anionic water solubilizing group, e.g., carboxy, sulfonate, sulfate, phosphate, or phosphonate. Specific examples include, but not limited to, alkylimino acetates, iminodialkanoates and aminoalkanoates, imidazolinium and ammonium derivatives. Other suitable amphoteric and zwitterionic emulsifying agents include betaines, sultaines, hydroxysultaines, alkyl sarcosinates, and alkanoyl sarcosinates.

Silicone emulsifying agents are typically organically modified organopoly siloxanes, sometimes called silicone surfactants. Useful silicone emulsifying agents include dimethicone copolyols. These materials are polydimethyl siloxanes, which have been modified to include polyether side chains such as polyethylene oxide chains, polypropylene oxide chains, mixtures of these chains, and polyether chains containing moieties derived from both ethylene oxide and propylene oxide.

Co-emulsifiers or secondary emulsifying agents include, but not limited to, polyoxylglycerides such as oleoyl macrogolglycerides (LABRAFIL® M 1944CS), linoleoyl macrogolglycerides (LABRAFIL® M 2125CS), caprylocaproyl macrogolglycerides (LABRASOL®), cetyl alcohol (and) ceteth-20 (and) steareth-20 (EMULCIRE™ 61 WL 2659), glyceryl stearate (and) PEG-75 stearate (GELOT® 64), d-alpha tocopheryl polyethylene glycol 1000 succinate (TPGS) and any mixtures thereof.

The term "solvent" refers to components that aid in the dissolution of the drug in the formulation. Solvents serve to maintain a solution of the drug in the composition. Some solvents can also enhance percutaneous penetration of drug and/or act as humectants. For topical corticosteroids, solvents can include water-immiscible substances such as fatty esters of natural fatty acids, triglycerides of animal or vegetable, medium chain triglycerides, mixtures of mono-, di- and/or triglycerides, waxes, hydrogenated vegetable oils, and mixtures thereof. Some specific examples include, but not limited to, castor oil, isopropyl myristate, dimethyl isosorbide, oleyl alcohol, labrafil, labrasol, medium chain triglyceride, diethyl sebacate, lanolin oil, citrate triisocetyl triglycerides having 10-18 carbon atoms, caprylic/capric triglycerides, coconut oil, corn oil, cottonseed oil, linseed oil, oil of mink, olive oil, palm oil, sunflower oil, nut oil, saturated paraffin oils, mineral oils, vegetable oils or glycerides, and the like. Solvent can also be selected from the group comprising monoalkyl ether of diethylene glycol such as diethylene glycol monomethyl ether, diethylene glycol monoethyl ether or mixtures thereof. In some embodiments, the solvent is diethylene glycol monoethyl ether. It is marketed by Gattefosse under the trade name TRANSCUTOL®, TRANSCUTOL-P®, TRANSCUTOL-CG®, and TRANSCUTOL-HP®.

In an embodiment, a solvent is selected from the group consisting of: mineral oil, isopropyl myristate, dimethyl isosorbide, oleyl Alcohol, labrafil, labrasol, medium chain triglyceride, diethyl sebacate, ammonium lauryl sulfate, lauramine oxide, sodium laureth sulfate, n-methyl-2-pyrrolidinone, octanoic_acid, cocobetaine, dimethylsulfoxide, sodium laureth 2 sulfate, benzyl_alcohol, ethylacetate, lactic acid, oleic acid, ethylacetate, spearmint oil, isostearic acid, ethanol, propylene glycol diacetate, dimethyl isosorbide, 1-butanol, methyl gluceth-10, sodium lauroylsarcosinate, polysorbate 20, isopropyl alcohol, 1-butanol, Capryol 90, sorbitanmonooleate, glyceryl ricinoleate, poloxamer, polyethylene glycol 200, polysorbate 65, triacetin, benzylalcohol, castor oil, arlacel 165, propylene glycol ricinoleate, glyceryl isostearate, propylene glycol, diethyl phthalate, glyceryl oleate, PEG-8 laurate, sorbitan sesquioleate, PPG-26 oleate, 1-octanol, Lauroglycol_FCC, diisopropyladipate, laureth 4, and diethyl sebacate. for solubilizing clobetasol propionate. The compositions of the present invention comprising from about 1% (w/w) to 30% (w/w) of solvent based on total weight of the composition.

The term "emollients" are substances that soften and soothe the skin. They are used to prevent dryness and scaling of the skin. Examples of emollients that can be used in the present invention include, but not limited to, oils of natural origin such as almond oil, coconut oil, olive oil, palm oil, peanut oil and the like, fatty acids such as lauric acid, myristic acid, palmitic acid, and stearic acid, monohydric alcohol esters of the fatty acids such as ethyl laurate, isopropyl laurate, ethyl myristate, n-propyl myristate, isopropyl myristate, ethyl palmitate, isopropyl palmitate, methyl palmitate, methyl stearate, ethyl stearate, isopropyl stearate, butyl stearate, isobutyl stearate, amyl stearate, and isoamyl stearate, glycols such as ethylene glycol, diethylene glycol, polyethylene glycol, branched aliphatic alcohols such as lauryl alcohol, myristyl alcohol, and stearyl alcohol, or mixtures thereof. Exemplary emollients include caprylic/capric triglycerides, castor oil, ceteareth-20, ceteareth-30, cetearyl alcohol, ceteth 20, cetostearyl alcohol, cetyl alcohol, cetyl stearyl alcohol, cocoa butter, diisopropyl adipate, glycerin, glyceryl monooleate, glyceryl monostearate, glyceryl stearate, isopropyl myristate, isopropyl palmitate, lanolin, lanolin alcohol, hydrogenated lanolin, liquid paraffins, linoleic acid, mineral oil, oleic acid, white petrolatum, polyethylene glycol, polyoxyethylene glycol fatty alcohol ethers, silicones and mixtures thereof.

Silicones are typically organically modified organopoly siloxanes, sometimes called silicone surfactants. Useful polysiloxane or silicone emollients include, but not limited to, polysiloxane polymer, dimethicone copolyols, cyclomethicones. These materials are polydimethyl siloxanes, which have been modified to include polyether side chains such as polyethylene oxide chains, polypropylene oxide chains, mixtures of these chains, and polyether chains containing moieties derived from both ethylene oxide and propylene oxide.

The term "antioxidants" are substances which inhibit oxidation or suppress reactions promoted by oxygen or peroxides. Antioxidants, especially lipid-soluble antioxidants, can be absorbed into the cellular membrane to neutralize oxygen radicals and thereby protect the membrane. Suitable antioxidants that can be used in the present invention include, but not limited to, ascorbic acid (vitamin C), glutathione, lipoic acid, uric acid, sorbic acid, carotenes, α-tocopherol (vitamin E), TPGS, ubiquinol, butylated hydroxyanisole, butylated hydroxytoluene, sodium benzoate, propyl gallate (PG, E310), and tertiary-butylhydroquinone.

The term "preservative" refers to a natural or synthetic chemical that prevents the decomposition of the composition by microbial growth or by undesirable chemical changes. Preservatives can desirably be incorporated into a composition for protecting against the growth of potentially harmful microorganisms. While microorganisms tend to grow in an aqueous phase and can also reside in a hydrophobic or oil phase. Examples of preservatives that can be used in the present invention include, but not limited to, methylparaben, propylparaben, benzyl alcohol, chlorocresol, benzalkonium chloride, cetrimonium chloride, sodium edetate, boric acid, sorbic acid, or any mixtures thereof.

The term "thickening agents" or "gelling agents" are used to give bulkiness to the composition. Examples of thickening agents or gelling agents that can be used in the present invention include, but not limited to carbomers, polyethylene glycols, acrylate polymers, methacrylate polymers, polyvinylpyrrolidones, copolymers based on butyl methacrylate and methyl methacrylate povidone, vinyl acetates, polyvinyl acetates, celluloses, gums, alginates, cellulose acetate phthalates, cellulose acetate butyrates, hydroxypropyl methyl cellulose phthalates, and the like. Examples include CARBOPOL® products, PEG 400, EUDRAGIT® 100, EUDRAGIT® RSPO, EUDRAGIT® RLPO, EUDRAGIT® ND40, PLASDONE®, copolymers based on butyl methacrylate and methyl methacrylate (PLASTOID® B), alkyl celluloses such as ethyl celluloses and methyl celluloses, hydroxyalkyl celluloses such as hydroxyethyl cellulose and hydroxypropyl cellulose, hydroxyalkyl alkyl celluloses such as hydroxypropyl methyl celluloses and hydroxybutyl methyl celluloses, gums such as xanthan gum, tragacanth, guar gum, locust bean gum, acacia, and the like.

In an embodiment, the thickening agents are non-polymeric thickening agents, examples of non-polymeric thickening agent are fatty alcohol selected from group comprising: cetyl alcohol, paraffin, stearyl alcohol, white wax, wax cetyl esters, microcrystalline wax, anionic emulsifying wax, nonionic emulsifying wax, yellow wax, castor oil, ceresin, cetostearyl alcohol, cyclomethicone, glyceryl behenate, hectorite, myristyl alcohol, cetylstearyl alcohol, triolein, and lanolin. Fatty alcohols that can be used as non-polymeric thickening agent, include but not limited to stearyl alcohol, oleyl alcohol, cetyl alcohol, cetostearyl alcohol are long chain fatty alcohols. Stearyl Alcohol is a white, waxy solid with a faint odor, while oleyl alcohol and octyl dodecanol are clear, colorless liquids. Oleyl alcohol is an unsaturated fatty alcohol, similar to the saturated fatty alcohols stearyl alcohol and cetyl alcohol. In an embodiment, the topical compositions of the present invention are substantially free of polymers.

Other thickening agents or gelling agents or polymers that are useful in the present invention include, but not limited to, polyamides, polycarbonates, polyalkylenes, polyalkylene glycols, polyalkylene oxides, polyalkylene terepthalates, polyvinyl alcohols, polyvinyl ethers, polyvinyl esters, polyvinyl halides, polyglycolides, polysiloxanes, polyurethanes and copolymers thereof, cellulose ethers, cellulose esters, nitrocelluloses, polymers of acrylic and methacrylic esters, cellulose acetates, cellulose propionates, cellulose acetate butyrates, cellulose acetate phthalates, carboxylethyl celluloses, cellulose triacetates, cellulose sulphate sodium salts, poly(methyl ethacrylate), poly(ethylmethacrylate), poly (butylmethacrylate), poly(isobutylmethacrylate), poly(hexylmethacrylate), poly(isodecylmethacrylate), poly(lauryl methacrylate), poly(phenyl methacrylate), poly(methyl acrylate), poly(isopropyl acrylate), poly(isobutyl acrylate), poly(octadecyl acrylate), polyethylenes, polypropylenes, poly(ethylene glycol), poly(ethylene oxide), poly(ethylene terephthalate), poly(vinyl alcohol), poly(vinyl acetate), poly (vinyl chloride), polystyrenes, and the like, including their mixtures thereof.

Examples of other useful polymers that can act as thickening agents or gelling agents include, but not limited to, synthetic polymers, such as polymers of lactic acid and glycolic acid, polyanhydrides, poly(ortho ester), polyurethanes, poly(butyric acid), poly(valeric acid), poly(caprolactone), poly(hydroxybutyrate), poly(lactide-co-glycolide), poly(lactide-co-caprolactone), and natural polymers such as alginate and other polysaccharides that include but not limited to arabinans, fructans, fucans, galactans, galacturonans, glucans, mannans, xylans (such as, for example, inulin), levan, fucoidan, carrageenan, galactocarolose, pectic acid, pectin, amylose, pullulan, glycogen, amylopectin, cellulose, dextran, pustulan, chitin, agarose, keratan, chondroitan, dermatan, hyaluronic acid, alginic acid, xanthan gum, starches, and various other natural homopolymers and heteropolymers, such as those containing one or more of aldoses, ketoses, acids or amines, erythrose, threose, ribose, arabinose, xylose, lyxose, allose, altrose, glucose, mannose, gulose, idose, galactose, talose, erythrulose, ribulose, xylulose, psicose, fructose, sorbose, tagatose, mannitol, sorbitol, lactose, sucrose, trehalose, maltose, cellobiose, glycine, serine, threonine, cysteine, tyrosine, asparagine, glutamine, aspartic acid, glutamic acid, lysine, arginine, histidine, glucuronic acid, gluconic acid, glucaric acid, galacturonic acid, mannuronic acid, glucosamine, galactosamine, and neuraminic acid, and naturally occurring derivatives thereof, and including dextran and cellulose, collagen, albumin and other hydrophilic proteins, zein and other prolamines and hydrophobic proteins, copolymers and mixtures thereof.

The term "humectant" refers to a hygroscopic substance that is often a molecule with several hydrophilic groups, most often hydroxyl groups, but amines and carboxyl groups, sometimes esterified, can be encountered as well; the affinity to form hydrogen bonds with molecules of water is crucial here. Examples of humectants include, but not limited to, glycerol, and glyceryl triacetate (E1518). Others can be sugar polyols like sorbitol (E420), xylitol and maltitol (E965), polymeric polyols like polydextrose (E1200), or natural extracts like quillaia (E999), lactic acid or urea.

Some of the excipients described above can have more than one function in a composition. For example, an excipient can be both a solvent and a penetration enhancer, or both a solvent and a carrier. The categorizations of excipients described above are not to be construed as limiting or restricting in any manner.

The composition of the present application can be applied directly onto affected areas of the skin, such as psoriatic plaques or dermatoses. Cream compositions, are applied in the form of film on the affected areas and, in embodiments, can provide release of the active agent for an extended duration of time.

In some embodiments, the topical composition of the present invention comprising: (a) a low dose of clobetasol; (b) an oil phase comprising: at least one penetration enhancing agent, and a non-polymeric thickening agent; (c) an aqueous phase; and (d) optionally, at least one pharmaceutically acceptable excipient; wherein the said topical composition comprising low dose of clobetasol has dose proportionate release rate as to be equivalent or more than the release rates of TEMOVATE® 0.05% cream. The term dose proportionate release rate as used herein means the topical composition of the present invention releases clobetasol such that concentration of clobetasol is equivalent to or more than the concentration delivered by 0.05% (w/w) topical clobetasol compositions such as TEMOVATE® cream. The dose proportionate release rate is cumulative percentage of drug release is at least about 6% of applied dose of clobetasol in about 9 hours.

In some embodiments, the topical composition of the present invention comprises a) a low-dose clobetasol; b) an oil phase comprising at least one penetration enhancing agent, and a non-polymeric thickening agent; and c) an aqueous phase; wherein the said composition provides a similar or improved therapeutic effect as compared to the topical composition comprising highest approved topical dose of clobetasol i.e. TEMOVATE®.

In some embodiments, the topical composition of the present invention comprises a) a low-dose clobetasol; b) an oil-in-water emulsion comprising a dispersed oil phase comprising at least one penetration enhancing agent, and a non-polymeric thickening agent, and a continuous aqueous phase; and c) one or more pharmaceutically acceptable excipients; wherein the said composition provides a similar or improved therapeutic effect as compared to the topical composition comprising highest approved topical dose of clobetasol i.e. TEMOVATE®.

In some embodiments, the topical composition of the present invention comprises low-dose clobetasol, wherein the composition provides a similar or an improved therapeutic effect and reduced adverse effect as compared to that of TEMOVATE®.

In some embodiments, the topical composition of the present invention comprises a low-dose clobetasol, wherein the composition provides a similar or an improved therapeutic effect and reduced adverse effect as compared to that of TEMOVATE®.

In some embodiments, the topical composition of the present invention comprises clobetasol provides lower percentage of reduction in serum concentration of dehydroepiandrosterone sulfate (DHEAS) and provides a similar or improved therapeutic effect as compared to that of TEMOVATE®.

In some embodiments, the topical composition of the present invention comprises a low-dose clobetasol, wherein the said composition provides lower percentage of reduction in serum concentration of dehydroepiandrosterone sulfate (DHEAS) and provides a similar or improved therapeutic effect as compared to that of TEMOVATE®.

In some embodiments, the topical composition of the present invention is oil-in-water emulsion or water-in-oil emulsion. In some embodiments, the topical composition comprising clobetasol is oil-in-water emulsion. In some embodiments, the topical composition is oil-in-water emulsion comprising (a) a dispersed oil phase comprising at least one skin penetration enhancing agent, a non-polymeric thickening agent and a continuous aqueous phase; and (b) one or more pharmaceutically acceptable excipients.

In some embodiments, the low-dose clobetasol is present in an amount from about 0.005% to about 0.04% of the total weight of the composition.

In some embodiments, the low-dose clobetasol is present in an amount from about 0.005% to about 0.04% of the total weight of the composition.

In some embodiments, the low dose clobetasol is about 10% less than the highest approved topical dose of clobetasol 0.05% (w/w), i.e. about 0.04% (w/w) based on total weight of the composition.

In some embodiments, the low dose clobetasol is about 20% less than the highest approved topical dose of clobetasol 0.05% (w/w), i.e. about 0.04% (w/w) based on total weight of the composition.

In some embodiments, the low dose clobetasol is about 30% less than the highest approved topical dose of clobetasol 0.05% (w/w), i.e. about 0.035% (w/w) based on total weight of the composition.

In some embodiments, the low dose clobetasol is about 40% less than the highest approved topical dose of clobetasol 0.05% (w/w), i.e. about 0.03% (w/w) based on total weight of the composition.

In some embodiments, the low dose clobetasol is about 50% less than the highest approved topical dose of clobetasol 0.05% (w/w), i.e. about 0.025% (w/w) based on total weight of the composition.

In some embodiments, the low dose clobetasol is about 60% less than the highest approved topical dose of clobetasol 0.05% (w/w), i.e. about 0.02% (w/w) based on total weight of the composition.

In some embodiments, the low dose clobetasol is about 70% less than the highest approved topical dose of clobetasol 0.05% (w/w), i.e. about 0.015% (w/w) based on total weight of the composition.

In some embodiments, the low dose clobetasol is about 80% less than the highest approved topical dose of clobetasol 0.05% (w/w), i.e. about 0.01% (w/w) based on total weight of the composition.

In some embodiments, the low dose clobetasol is about 90% less than the highest approved topical dose of clobetasol 0.05% (w/w), i.e. about 0.005% (w/w) based on total weight of the composition.

In a preferred aspect, the low-dose clobetasol is about 50% less than the highest approved topical dose of clobetasol 0.05%, i.e. about 0.025% (w/w) based on total weight of the composition.

In some embodiments, the topical composition comprises a low dose clobetasol of about 0.025% (w/w) provides equivalent therapeutic efficacy of highest approved topical dose of clobetasol of 0.05% (w/w).

In some aspects of the present invention, the clobetasol is clobetasol propionate i.e. clobetasol-17-propionate.

In some aspects of the present invention, the clobetasol is clobetasol propionate i.e. clobetasol-17-propionate and the clobetasol propionate concentration is in the amount of about 0.025% (w/w).

In some embodiments, the topical composition of the present invention provides a similar or improved therapeutic efficacy and/or reduced adverse effect of clobetasol. In some embodiments, the topical composition of the present invention provides a similar or improved therapeutic efficacy and/or reduced adverse effect of clobetasol propionate.

In some embodiments, the topical composition of the present invention comprises a) about 0.025% (w/w) of clobetasol; b) an oil phase comprising at least one penetration enhancing agent, and a non-polymeric thickening agent; and c) an aqueous phase; wherein the said composition provides a similar or improved therapeutic effect as compared to that of the topical composition comprising highest approved topical dose of clobetasol i.e. TEMOVATE®.

In some embodiments, the topical cream composition of the present invention comprises a) about 0.025% (w/w) of clobetasol propionate; b) an oil phase comprising at least one penetration enhancing agent, and a non-polymeric thickening agent; and c) an aqueous phase; wherein the said composition provides a similar or improved therapeutic effect as compared to that of the topical composition comprising highest approved topical dose of clobetasol i.e. TEMOVATE® cream.

In some embodiments, the topical composition of the present invention comprises a) about 0.025% (w/w) of clobetasol; b) an oil phase comprising at least one penetration enhancing agent, and a non-polymeric thickening agent; and c) an aqueous phase; wherein the said composition provides a similar or improved therapeutic effect as compared to that of the topical composition comprising highest approved topical dose of clobetasol i.e. TEMOVATE® and the said composition provides mean clobetasol plasma concentrations less than about 130 pg/mL. In another embodiment TEMOVATE® is TEMOVATE® cream.

In some embodiments, the topical composition of the present invention comprises a) about 0.025% (w/w) of clobetasol propionate; b) an oil phase comprising at least one penetration enhancing agent, and a non-polymeric thickening agent; and c) an aqueous phase; wherein the said composition provides a similar or improved therapeutic effect as compared to that of the topical composition comprising highest approved topical dose of clobetasol i.e. TEMOVATE® and the said composition provides mean clobetasol propionate plasma concentrations less than about 130 pg/mL. In another embodiment TEMOVATE® is TEMOVATE® cream.

In some embodiments, the topical composition of the present invention comprises a) about 0.025% (w/w) of clobetasol; b) an oil phase comprising at least one penetration enhancing agent, and a non-polymeric thickening agent; and c) an aqueous phase; wherein the said composition provides a similar or improved therapeutic effect as compared to that of the topical composition comprising highest approved topical dose of clobetasol i.e. TEMOVATE® and the said composition provides post treatment mean clobetasol plasma levels less than about 150 pg/mL. In another embodiment TEMOVATE® is TEMOVATE® cream.

In some embodiments, the topical composition of the present invention comprises a) about 0.025% (w/w) of clobetasol propionate; b) an oil phase comprising at least one penetration enhancing agent, and a non-polymeric thickening agent; and c) an aqueous phase; wherein the said composition provides a similar or improved therapeutic effect as compared to that of the topical composition comprising highest approved topical dose of clobetasol i.e. TEMOVATE® and the said composition provides post treatment mean clobetasol propionate plasma levels less than about 150 pg/mL. In another embodiment TEMOVATE® is TEMOVATE® cream.

In some embodiments, the topical composition of the present invention comprises a) about 0.025% (w/w) of clobetasol propionate; b) an oil phase comprising at least one penetration enhancing agent, and a non-polymeric thickening agent; and c) an aqueous phase; wherein the said composition provides a similar or improved therapeutic effect as compared to that of the topical composition comprising highest approved topical dose of clobetasol i.e. TEMOVATE® and the said composition provides post treatment mean clobetasol propionate plasma levels from about 130 pg/mL to about 10 pg/ml. In another embodiment TEMOVATE® is TEMOVATE® cream.

In some embodiments, the topical composition of the present invention comprises a) about 0.025% (w/w) of clobetasol propionate; b) an oil-in-water emulsion comprising a dispersed oil phase comprising at least one penetration enhancing agent, and a non-polymeric thickening agent, and a continuous aqueous phase; and c) one or more pharmaceutically acceptable excipients; wherein the said composition provides a similar or improved therapeutic effect as compared to the topical composition comprising highest approved topical dose of clobetasol i.e. TEMOVATE®.

In some embodiments, the topical composition of the present invention comprises a) about 0.025% (w/w) of clobetasol propionate; b) an oil-in-water emulsion comprising a dispersed oil phase comprising at least one penetration enhancing agent, and a non-polymeric thickening agent, and a continuous aqueous phase; and c) one or more pharmaceutically acceptable excipients; wherein the said composition provides a similar or improved therapeutic effect as compared to the topical composition comprising highest approved topical dose of clobetasol i.e. TEMOVATE® and the said composition provides mean clobetasol propionate plasma levels less than about 130 pg/mL. In another embodiment TEMOVATE® is TEMOVATE® cream.

In some embodiments, the topical composition of the present invention comprises a) about 0.025% (w/w) of clobetasol propionate; b) an oil-in-water emulsion comprising a dispersed oil phase comprising at least one penetration enhancing agent, and a non-polymeric thickening agent, and a continuous aqueous phase; and c) one or more pharmaceutically acceptable excipients; wherein the said composition provides a similar or improved therapeutic effect as compared to the topical composition comprising highest approved topical dose of clobetasol and the said composition provides post treatment mean clobetasol propionate plasma levels less than about 150 pg/mL. In another embodiment TEMOVATE® is TEMOVATE® cream.

In some embodiments, the topical composition of the present invention comprises a) about 0.025% (w/w) of clobetasol propionate; b) an oil-in-water emulsion comprising a dispersed oil phase comprising at least one penetration enhancing agent, and a non-polymeric thickening agent, and a continuous aqueous phase; and c) one or more pharmaceutically acceptable excipients; wherein the said composition provides a similar or improved therapeutic effect as compared to the topical composition comprising highest approved topical dose of clobetasol i.e. TEMOVATE® and the said composition provides post treatment mean clobetasol propionate plasma levels from about 130 pg/mL to about 10 pg/ml. In another embodiment TEMOVATE® is TEMOVATE® cream.

In some embodiments, the adverse effect of clobetasol is adverse effect of endocrine system. In some embodiments, the adverse effect of endocrine system is HPA axis suppression.

In some embodiments, the adverse effect of clobetasol is reduction in serum concentration of dehydroepiandrosterone (DHEA) and/or dehydroepiandrosterone sulfate (DHEAS).

In some embodiments of the present invention TEMOVATE® is TEMOVATE® cream.

In some embodiments, the topical compositions of the present invention comprises 0.025% (w/w) clobetasol, provides lower percentage reduction of serum concentration of DHEAS. The percentage reduction of DHEAS serum concentration is less than about 18% or is less than about 15% or is less than about 10% or is less than about 5%. In some embodiments, 0.025% (w/w) clobetasol of the present invention provides the percentage reduction of DHEAS serum concentration is about 18% or 17% or 16% or 15% or 14% or 13% or 12% or 11% or 10% or 9% or 8% or 7% or 6% or 5% or 4% or 3% or 2% or 1%, wherein the percentage reduction of serum concentration of DHEAS is lower than that of TEMOVATE®.

In some embodiments, the topical compositions of the present invention comprises 0.025% (w/w) clobetasol, provides the percentage reduction of DHEAS serum concentration is at least about 20% or is at least about 30% or is at least about 40% or is at least about 55%, when compared to that of TEMOVATE®.

In some embodiments, the topical compositions of the present invention comprises 0.025% (w/w) clobetasol propionate, provides lower percentage reduction of serum concentration of DHEAS. The percentage reduction of DHEAS serum concentration is less than about 18% or is less than about 15% or is less than about 10% or is less than about 5%. In some embodiments, 0.025% (w/w) clobetasol propionate of the present invention provides the percentage reduction of DHEAS serum concentration is about 18% or 17% or 16% or 15% or 14% or 13% or 12% or 11% or 10% or 9% or 8% or 7% or 6% or 5% or 4% or 3% or 2% or 1%, wherein the percentage reduction of serum concentration of DHEAS is lower than that of TEMOVATE®.

In some embodiments, the topical compositions of the present invention comprises 0.025% (w/w) clobetasol propionate, provides the percentage reduction of DHEAS serum concentration is at least about 20% or is at least about 30% or is at least about 40% or is at least about 55% when compared to that of TEMOVATE® cream.

In some embodiments, the topical compositions of the present invention comprises from about 0.005% (w/w) to about 0.04% (w/w) clobetasol, provides the percentage reduction of DHEAS serum concentration is about 18% or 17% or 16% or 15% or 14% or 13% or 12% or 11% or 10% or 9% or 8% or 7% or 6% or 5% or 4% or 3% or 2% or 1%, wherein the percentage reduction of serum concentration of DHEAS is lower than that of TEMOVATE®.

In some embodiments, the topical compositions of the present invention comprises about 0.025% (w/w) clobetasol, provides lower percentage of reduction of DHEAS serum concentration as compared to that of TEMOVATE®.

In some embodiments, the topical composition of the present invention comprises 25% (w/w) clobetasol provides therapeutically beneficial effects of clobetasol which is substantially free of adverse effect of clobetasol wherein the said adverse effect is HPA axis suppression and/or reduction in serum concentration of dehydroepiandrosterone (DHEA) and/or dehydroepiandrosterone sulfate (DHEAS).

In some embodiments, the topical composition of the present invention comprises a low-dose clobetasol, wherein the said composition provides substantially free of HPA axis suppression in a subject.

In some embodiments, the topical composition of the present invention comprises about 0.025% (w/w) clobetasol, wherein the said composition provides substantially free of HPA axis suppression in a subject.

In some embodiments, the topical composition of the present invention comprises about 0.025% (w/w) clobetasol, wherein the said composition provides substantially free of HPA axis suppression, when compared to that of TEMOVATE®.

In some embodiments, the topical composition of the present invention comprises about 0.025% (w/w) clobetasol propionate, wherein the said composition provides substantially free of HPA axis suppression in a subject.

In some embodiments, the topical composition of the present invention comprises about 0.025% (w/w) clobetasol propionate, wherein the said composition provides substantially free of HPA axis suppression, when compared to that of TEMOVATE®.

In some embodiments, the topical composition of the present invention comprises about 0.025% (w/w) clobetasol propionate, wherein the said composition provides post treatment mean plasma concentration of clobetasol propionate less than about 150 pg/ml, and provides substantially free of HPA axis suppression, when compared to that of TEMOVATE®.

In some embodiments, the topical composition of the present invention comprises a low-dose clobetasol, wherein the said composition provides lower percentage reduction of serum concentration of DHEAS, when compared to that of TEMOVATE®.

In some embodiments, the topical composition of the present invention comprises 0.025% (w/w) clobetasol, wherein the said composition provides lower percentage reduction of serum concentration of DHEAS, when compared to that of TEMOVATE®. In some embodiments, the percentage reduction is less than about 15%

In some embodiments, the topical composition of the present invention comprises 0.025% (w/w) clobetasol propionate, wherein the said composition provides lower percentage reduction of serum concentration of DHEAS, when compared to that of TEMOVATE®. In some embodiments, the percentage reduction is less than about 15%

In some embodiments, the topical composition of the present invention comprises about 0.025% (w/w) clobetasol, wherein the said composition provides lower percentage of reduction of serum concentration of DHEAS, when compared to that of TEMOVATE®. In some embodiments, the topical composition of the present invention comprises about 0.025% (w/w) clobetasol propionate, wherein the said composition provides post treatment mean plasma concentration of clobetasol propionate less than about 150 pg/ml, and provides lower percentage of reduction of serum concentration of DHEAS, when compared to that of TEMOVATE®.

In some embodiments, the topical composition of the present invention comprises about 0.025% (w/w) clobetasol, wherein the said composition provides post treatment mean plasma concentration of clobetasol less than about 150 pg/ml, and provides lower percentage of reduction of serum concentration of DHEAS and further provides substantially free of HPA axis suppression, when compared to that of TEMOVATE®

In some embodiments, the topical composition of the present invention comprises about 0.025% (w/w) clobetasol propionate, wherein the said composition provides post treatment mean plasma concentration of clobetasol propionate less than about 150 pg/ml, and provides lower percentage of reduction of serum concentration of DHEAS and further provides substantially free of HPA axis suppression, when compared to that of TEMOVATE®

In some embodiments, the percentage reduction in DHEA or DHEAS serum levels is a parameter for adverse effect of steroid drug such as clobetasol. The topical compositions of the present invention provides lower percentage reduction in serum concentration of DHEA or DHEAS.

In some embodiments, the topical composition of the present invention comprises a) a low-dose clobetasol; b) an oil phase comprising at least one penetration enhancing agent, and a non-polymeric thickening agent; and c) an aqueous phase; which provides a similar or improved therapeutic effect of highest approved topical dose of clobetasol i.e. TEMOVATE® and provides substantially free of adverse effect, wherein the adverse effect is effect on endocrine system such as adrenal gland which in turn causes HPA axis suppression.

In some embodiments, the topical composition of the present invention comprises a) a low-dose clobetasol; b) an oil phase comprising at least one penetration enhancing agent, and a non-polymeric thickening agent; and c) an aqueous phase; which provides a similar or improved therapeutic effect of highest approved topical dose of clobetasol i.e. TEMOVATE® and provides substantially free of adverse effect, wherein the adverse effect is reduced levels of dehydroepiandrosterone sulfate (DHEAS).

In some embodiments, the topical composition of the present invention comprises a) about 0.025% (w/w) clobetasol; b) an oil phase comprising at least one penetration enhancing agent, and a non-polymeric thickening agent; and c) an aqueous phase; which provides a similar or improved therapeutic effect of highest approved topical dose of clobetasol i.e. TEMOVATE® and provides substantially free of adverse effect, wherein the adverse effect is effect on endocrine system such as adrenal gland which in turn causes HPA axis suppression.

In some embodiments, the topical composition of the present invention comprises a) about 0.025% (w/w) clobetasol; b) an oil phase comprising at least one penetration enhancing agent, and a non-polymeric thickening agent; and c) an aqueous phase; which provides a similar or improved therapeutic effect of highest approved topical dose of clobetasol i.e. TEMOVATE® and provides substantially free of adverse effect, wherein the adverse effect is reduced levels of dehydroepiandrosterone sulfate (DHEAS).

In some embodiments, the topical composition of the present invention comprises a) about 0.025% (w/w) clobetasol propionate; b) an oil phase comprising at least one penetration enhancing agent, and a non-polymeric thickening agent; and c) an aqueous phase; which provides a similar or improved therapeutic effect of highest approved topical dose of clobetasol i.e. TEMOVATE® and provides substantially free of adverse effect, wherein the adverse effect is effect on endocrine system such as adrenal gland which in turn causes HPA axis suppression.

In some embodiments, the topical composition of the present invention comprises a) about 0.025% (w/w) clobetasol propionate; b) an oil phase comprising at least one penetration enhancing agent, and a non-polymeric thickening agent; and c) an aqueous phase; which provides a similar or improved therapeutic effect of highest approved topical dose of clobetasol i.e. TEMOVATE® and provides substantially free of adverse effect, wherein the said adverse effect is reduced levels of dehydroepiandrosterone sulfate (DHEAS).

In some embodiments, the topical composition of the present invention comprises a) about 0.025% (w/w) clobetasol propionate; b) an oil phase comprising at least one penetration enhancing agent, and a non-polymeric thickening agent; and c) an aqueous phase; which provides a similar or improved therapeutic effect of highest approved topical dose of clobetasol i.e. TEMOVATE® and provides substantially free of adverse effects, wherein the adverse effects are HPA axis suppression and reduced levels of dehydroepiandrosterone sulfate (DHEAS).

In some embodiments, the topical composition of the present invention comprises a) about 0.025% (w/w) clobetasol propionate; b) an oil phase comprises at least one penetration enhancing agent, and a non-polymeric thickening agent; and c) an aqueous phase; which provides a similar or improved therapeutic effect of highest approved topical dose of clobetasol i.e. TEMOVATE® and provides substantially free of adverse effects, wherein the adverse effects are HPA axis suppression and reduced levels of dehydroepiandrosterone sulfate (DHEAS).

In some embodiments, the topical composition of the present invention comprises a) a low-dose clobetasol; b) an oil phase comprising at least one penetration enhancing agent, and a non-polymeric thickening agent; and c) an aqueous phase; which provides a similar or improved therapeutic effect of highest approved topical dose of clobetasol i.e. TEMOVATE® and provides mean clobetasol plasma levels insufficient to reduce serum levels of cortisol less than or equal to about 18 ug/dL.

In some embodiments, the topical composition of the present invention comprises a) about 0.025% (w/w) clobetasol; b) an oil phase comprising at least one penetration enhancing agent, and a non-polymeric thickening agent; and c) an aqueous phase; which provides a similar or improved therapeutic effect of highest approved topical dose of clobetasol i.e. TEMOVATE® and provides mean clobetasol plasma levels insufficient to reduce serum levels of cortisol less than or equal to about 18 ug/dL.

In some embodiments, the topical composition of the present invention comprises a) about 0.025% (w/w) clobetasol propionate; b) an oil phase comprising at least one penetration enhancing agent, and a non-polymeric thickening agent; and c) an aqueous phase; which provides a similar or improved therapeutic effect of highest approved topical dose of clobetasol i.e. TEMOVATE® and provides mean clobetasol propionate plasma levels insufficient to reduce serum levels of cortisol less than or equal to about 18 ug/dL.

In some embodiments, the topical composition of present invention comprises about 0.025% (w/w) clobetasol, wherein the said composition provides the post treatment mean clobetasol plasma concentration is significantly lower than that of TEMOVATE®, and the mean plasma concentrations are measured post 2 weeks treatment period.

In some embodiments, the topical composition of present invention comprises about 0.025% (w/w) clobetasol propionate, wherein the said composition provides the post treatment mean clobetasol propionate plasma concentration is significantly lower than that of TEMOVATE®, and the mean plasma concentrations are measured post two weeks treatment period.

In some embodiments, post treatment plasm concentrations are measured post 8 weeks treatment period.

In some embodiments, post treatment plasm concentrations are measured post 4 weeks treatment period.

In some embodiments, post treatment plasm concentrations are measured post 15 days treatment period.

In some embodiments, the topical composition of present invention comprises about 0.025% (w/w) of clobetasol propionate, wherein the said composition provides the post treatment mean plasma concentration is significantly lower than that of TEMOVATE®. The mean plasma concentrations are measured post 15 days or two weeks treatment. In some embodiments, the post treatment mean clobetasol propionate plasma levels are less than about 150 pg/ml. In some aspects, the post treatment mean clobetasol propionate plasma levels are less than about 130 pg/ml, or the post treatment mean clobetasol propionate plasma levels are less than about 100 pg/ml or the post treatment mean clobetasol propionate plasma levels are less than about 75 pg/ml or the post treatment mean clobetasol propionate plasma levels are less than about 50 pg/ml or the post treatment mean clobetasol propionate plasma levels are less than about 25 pg/ml or the post treatment mean clobetasol propionate plasma levels are below quantifiable level. In some embodiments, the topical composition of present invention comprises from about 0.005% (w/w) to about 0.04% (w/w) of clobetasol, wherein the said composition provides the post treatment mean plasma concentration is significantly lower than that of TEMOVATE®, and the mean plasma concentrations are measured post eight weeks treatment or post four weeks treatment or post two weeks treatment.

In some embodiments, the topical composition of the present invention comprises a) about 0.025% (w/w) clobetasol; b) an oil phase comprising at least one penetration enhancing agent, and a non-polymeric thickening agent; and c) an aqueous phase; which provides a similar or improved therapeutic effect of highest approved topical dose of clobetasol i.e. TEMOVATE® and provides mean clobetasol plasma levels in the range of from about 130 pg/mL to 0 pg/mL.

In some embodiments, the topical composition of the present invention comprises a) about 0.025% (w/w) clobetasol; b) an oil-in-water emulsion comprising a dispersed oil phase comprising at least one penetration enhancing agent, and a non-polymeric thickening agent, and a continuous aqueous phase; and c) one or more pharmaceutically acceptable excipients; which provides a similar or improved therapeutic effect of highest approved topical dose of clobetasol i.e. TEMOVATE® and provides mean clobetasol plasma levels in the range of from about 130 pg/mL to 0 pg/mL.

In some embodiments, the topical composition of the present invention comprises a) about 0.025% (w/w) clobetasol propionate; b) an oil phase comprising at least one penetration enhancing agent, and a non-polymeric thickening agent; and c) an aqueous phase; which provides a similar or improved therapeutic effect of highest approved topical dose of clobetasol i.e. TEMOVATE® and provides mean clobetasol propionate plasma levels in the range of from about 130 pg/mL to 0 pg/mL.

In some embodiments, the topical composition of the present invention comprises a) about 0.025% (w/w) clobetasol propionate; b) an oil-in-water emulsion comprising a dispersed oil phase comprising at least one penetration enhancing agent, and a non-polymeric thickening agent, and a continuous aqueous phase; and c) one or more pharmaceutically acceptable excipients; which provides a similar or improved therapeutic effect of highest approved topical dose of clobetasol i.e. TEMOVATE® and provides mean clobetasol propionate plasma levels in the range of from about 130 pg/mL to 0 pg/mL. In some embodiments, clobetasol propionate plasma levels are in the range of from about 120 pg/mL to about 20 pg/mL or in the range of 100 pg/mL to 20 pg/mL or In some embodiments, the topical composition of the present invention comprises a) about 0.025% (w/w) clobetasol propionate; b) an oil-in-water emulsion comprising a dispersed oil phase comprising at least one penetration enhancing agent, and a non-polymeric thickening agent, and a continuous aqueous phase; and c) one or more pharmaceutically acceptable excipients; which provides a similar or improved therapeutic effect of TEMOVATE® and provides post treatment mean clobetasol propionate plasma levels in the range of from about 150 pg/mL to 0 pg/mL. In some embodiments, clobetasol propionate plasma levels are in the range of about 130 pg/mL to 0 pg/mL or about 100 pg/mL to about 10 pg/mL.

In some embodiments, the composition of the present invention provides mean plasma concentration which is insufficient to cause clinically significant HPA axis suppression.

In some embodiments, the composition of the present invention provides mean plasma concentration which provides lower percentage reduction in serum levels of DHEAS In some embodiments, the composition of the present invention provides mean plasma concentrations which causes substantially free of HPA axis suppression and provides lower percentage reduction in serum levels of DHEAS.

In some embodiments, the topical composition of the present invention comprises a low-dose clobetasol provides post treatment mean clobetasol plasma concentration, which causes substantially free of HPA axis suppression. and/or lower percentage reduction in serum levels of DHEAS.

In some embodiments, the topical composition of the present invention comprises about 0.025% (w/w) clobetasol provides post treatment mean clobetasol plasma concentration, which causes substantially free of HPA axis suppression; and/or lower percentage reduction in serum levels of DHEAS.

In some embodiments, the topical composition of the present invention comprises about 0.025% (w/w) clobetasol propionate provides post treatment mean clobetasol plasma concentration, which causes substantially free of HPA axis suppression; and/or lower percentage reduction in serum levels of DHEAS.

In some embodiments, the topical composition of the present invention comprises about 0.025% (w/w) clobetasol propionate provides post treatment mean clobetasol propionate plasma concentration, which causes substantially free of HPA axis suppression; or lower percentage reduction in serum levels of DHEAS.

In some embodiments, the topical composition of present invention comprises about 0.025% (w/w) clobetasol propionate provides mean clobetasol propionate plasma levels less than or equal to about 130 pg/ml or 129 or 128 or 127 or 126 or 125 or 124 or 123 or 122 or 121 or 120 or 119 or 118 or 117 or 116 or 115 or 114 or 113 or 112 or 111 or 110 or 109 or 108 or 107 or 106 or 105 or 104 or 103 or 102 or 101 or 100 or 99 or 98 or 97 or 96 or 95 or 94 or 93 or 92 or 91 or 90 or 89 or 88 or 87 or 86 or 85 or 84 or 83 or 82 or 81 or 80 or 79 or 78 or 77 or 76 or 75 or 74 or 73 or 72 or 71 or 70 or 69 or 68 or 67 or 66 or 65 or 64 or 63 or 62 or 61 or 60 or 59 or 58 or 57 or 56 or 55 or 54 or 53 or 52 or 51 or 50 or 49 or 48 or 47 or 46 or 45 or 44 or 43 or 42 or 41 or 40 or 39 or 38 or 37 or 36 or 35 or 34 or 33 or 32 or 31 or 30 or 29 or 28 or 27 or 26 or 25 or 24 or 23 or 22 or 21 or 20 or 19 or 18 or 17 or 16 or 15 or 14 or 13 or 12 or 11 or 10 or 9 or 8 or 7 or 6 or 5 or 4 or 3 or 2 or 1 or 0 pg/mL in a subject when administered for 15 days and provides substantially free of HPA axis suppression.

In some embodiments, the topical composition of present invention comprises about 0.025% (w/w) clobetasol propionate provides mean clobetasol propionate plasma levels less than or equal to about 130 pg/ml or 129 or 128 or 127 or 126 or 125 or 124 or 123 or 122 or 121 or 120 or 119 or 118 or 117 or 116 or 115 or 114 or 113 or 112 or 111 or 110 or 109 or 108 or 107 or 106 or 105 or 104 or 103 or 102 or 101 or 100 or 99 or 98 or 97 or 96 or 95 or 94 or 93 or 92 or 91 or 90 or 89 or 88 or 87 or 86 or 85 or 84 or 83 or 82 or 81 or 80 or 79 or 78 or 77 or 76 or 75 or 74 or 73 or 72 or 71 or 70 or 69 or 68 or 67 or 66 or 65 or 64 or 63 or 62 or 61 or 60 or 59 or 58 or 57 or 56 or 55 or 54 or 53 or 52 or 51 or 50 or 49 or 48 or 47 or 46 or 45 or 44 or 43 or 42 or 41 or 40 or 39 or 38 or 37 or 36 or 35 or 34 or 33 or 32 or 31 or 30 or 29 or 28 or 27 or 26 or 25 or 24 or 23 or 22 or 21 or 20 or 19 or 18 or 17 or 16 or 15 or 14 or 13 or 12 or 11 or 10 or 9 or 8 or 7 or 6 or 5 or 4 or 3 or 2 or 1 or 0 pg/mL in a subject when administered for 15 days and provides lower percentage reduction in DHEAS serum concentration.

In some embodiments, the topical composition of present invention comprises about 0.025% (w/w) clobetasol propionate provides post treatment mean clobetasol propionate plasma concentration less than or equal to about 150 pg/ml or 149 or 148 or 147 or 146 or 145 or 144 or 143 or 142 or 141 or 140 or 139 or 138 or 137 or 136 or 135 or 134 or 133 or 132 or 131 or 131 or 129 or 128 or 127 or 126 or 125 or 124 or 123 or 122 or 121 or 120 or 119 or 118 or 117 or 116 or 115 or 114 or 113 or 112 or 111 or 110 or 109 or 108 or 107 or 106 or 105 or 104 or 103 or 102 or 101 or 100 or 99 or 98 or 97 or 96 or 95 or 94 or 93 or 92 or 91 or 90 or 89 or 88 or 87 or 86 or 85 or 84 or 83 or 82 or 81 or 80 or 79 or 78 or 77 or 76 or 75 or 74 or 73 or 72 or 71 or 70 or 69 or 68 or 67 or 66 or 65 or 64 or 63 or 62 or 61 or 60 or 59 or 58 or 57 or 56 or 55 or 54 or 53 or 52 or 51 or 50 or 49 or 48 or 47 or 46 or 45 or 44 or 43 or 42 or 41 or 40 or 39 or 38 or 37 or 36 or 35 or 34 or 33 or 32 or 31 or 30 or 29 or 28 or 27 or 26 or 25 or 24 or 23 or 22 or 21 or 20 or 19 or 18 or 17 or 16 or 15 or 14 or 13 or 12 or 11 or 10 or 9 or 8 or 7 or 6 or 5 or 4 or 3 or 2 or 1 or 0 pg/mL in a subject when administered for 15 days, and provides substantially free of HPA axis suppression.

In some embodiments, the topical composition of present invention comprises about 0.025% (w/w) clobetasol propionate provides post treatment mean clobetasol propionate plasma concentration less than or equal to about 150 pg/ml or 149 or 148 or 147 or 146 or 145 or 144 or 143 or 142 or 141 or 140 or 139 or 138 or 137 or 136 or 135 or 134 or 133 or 132 or 131 or 131 or 129 or 128 or 127 or 126 or 125 or 124 or 123 or 122 or 121 or 120 or 119 or 118 or 117 or 116 or 115 or 114 or 113 or 112 or 111 or 110 or 109 or 108 or 107 or 106 or 105 or 104 or 103 or 102 or 101 or 100 or 99 or 98 or 97 or 96 or 95 or 94 or 93 or 92 or 91 or 90 or 89 or 88 or 87 or 86 or 85 or 84 or 83 or 82 or 81 or 80 or 79 or 78 or 77 or 76 or 75 or 74 or 73 or 72 or 71 or 70 or 69 or 68 or 67 or 66 or 65 or 64 or 63 or 62 or 61 or 60 or 59 or 58 or 57 or 56 or 55 or 54 or 53 or 52 or 51 or 50 or 49 or 48 or 47 or 46 or 45 or 44 or 43 or 42 or 41 or 40 or 39 or 38 or 37 or 36 or 35 or 34 or 33 or 32 or 31 or 30 or 29 or 28 or 27 or 26 or 25 or 24 or 23 or 22 or 21 or 20 or 19 or 18 or 17 or 16 or 15 or 14 or 13 or 12 or 11 or 10 or 9 or 8 or 7 or 6 or 5 or 4 or 3 or 2 or 1 or 0 pg/mL in a subject when administered for 15 days, and provides lower percentage reduction in DHEAS serum concentration.

In some embodiments, the topical composition of the present invention comprises a) about 0.025% (w/w) clobetasol propionate; b) an oil phase comprising at least one penetration enhancing agent, and a non-polymeric thickening agent; and c) an aqueous phase; which provides a similar or improved therapeutic effect of highest approved topical dose of clobetasol i.e. TEMOVATE® and provides median clobetasol propionate plasma levels insufficient to reduce serum levels of cortisol less than or equal to about 18 ug/dL.

In some embodiments, the present invention relates to a method for prophylaxis, amelioration, or treatment of psoriasis, relief of the inflammatory and pruritic manifestations of steroid responsive dermatoses, erythema, contact sensitivity reactions, and other associated diseases or disorders, by administering to a subject, comprising administration a low-dose clobetasol, to the affected area of the skin once or twice daily at least for one day; wherein the said composition provides a similar or improved therapeutic effect of highest approved topical dose of clobetasol i.e. TEMOVATE® and provides substantially free of HPA axis suppression. In some embodiments, low-dose clobetasol is about 0.025% (w/w) clobetasol. In some embodiments, low-dose clobetasol is about 0.025% (w/w) clobetasol propionate.

In some embodiments, the present invention relates to a method for prophylaxis, amelioration, or treatment of psoriasis, relief of the inflammatory and pruritic manifestations of steroid responsive dermatoses, erythema, contact sensitivity reactions, and other associated diseases or disorders, by administering to a subject, comprising administration a low-dose clobetasol, to the affected area of the skin once or twice daily up to about two weeks; wherein the said composition provides a similar or improved therapeutic effect of highest approved topical dose of clobetasol i.e. TEMOVATE® and provides substantially free of HPA axis suppression. In some embodiments, low-dose clobetasol is about 0.025% (w/w) clobetasol. In some embodiments, low-dose clobetasol is about 0.025% (w/w) clobetasol propionate.

In some embodiments, the present invention relates to a method for prophylaxis, amelioration, or treatment of psoriasis, relief of the inflammatory and pruritic manifestations of steroid responsive dermatoses, erythema, contact sensitivity reactions, and other associated diseases or disorders, by administering to a subject, comprising administration a low-dose clobetasol, to the affected area of the skin once or twice daily up to about four weeks; wherein the said composition provides a similar or improved therapeutic effect of highest approved topical dose of clobetasol i.e. TEMOVATE® and provides substantially free of HPA axis suppression. In some embodiments, low-dose clobetasol is about 0.025% (w/w) clobetasol. In some embodiments, low-dose clobetasol is about 0.025% (w/w) clobetasol propionate.

In some embodiments, the present invention relates to a method for prophylaxis, amelioration, or treatment of psoriasis, relief of the inflammatory and pruritic manifestations of steroid responsive dermatoses, erythema, contact sensitivity reactions, and other associated diseases or disorders, by administering to a subject, comprising administration a low-dose clobetasol, to the affected area of the skin once or twice daily at least for one day; wherein the said composition provides a similar or improved therapeutic effect of highest approved topical dose of clobetasol i.e. TEMOVATE® and provides lower percentage of reduction in DHEAS. In some embodiments, low-dose clobetasol is about 0.025% (w/w) clobetasol. In some embodiments, low-dose clobetasol is about 0.025% (w/w) clobetasol propionate.

In some embodiments, the present invention relates to a method for prophylaxis, amelioration, or treatment of psoriasis, relief of the inflammatory and pruritic manifestations of steroid responsive dermatoses, erythema, contact sensitivity reactions, and other associated diseases or disorders, by administering to a subject, comprising administration a low-dose clobetasol, to the affected area of the skin once or twice daily up to about two weeks; wherein the said composition provides a similar or improved therapeutic effect of highest approved topical dose of clobetasol i.e. TEMOVATE® and provides lower percentage of reduction in DHEAS. In some embodiments, low-dose clobetasol is about 0.025% (w/w) clobetasol. In some embodiments, low-dose clobetasol is about 0.025% (w/w) clobetasol propionate.

In some embodiments, the present invention relates to a method for prophylaxis, amelioration, or treatment of psoriasis, relief of the inflammatory and pruritic manifestations of steroid responsive dermatoses, erythema, contact sensitivity reactions, and other associated diseases or disorders, by administering to a subject, comprising administration a low-dose clobetasol, to the affected area of the skin once or twice daily up to about four weeks; wherein the said composition provides a similar or improved therapeutic effect of highest approved topical dose of clobetasol i.e. TEMOVATE® and provides lower percentage of reduction in DHEAS. In some embodiments, low-dose clobetasol is about 0.025% (w/w) clobetasol. In some embodiments, low-dose clobetasol is about 0.025% (w/w) clobetasol propionate.

In some embodiments, the method of treating psoriasis in a subject, the said method comprises topical administration of a composition comprising a low-dose of clobetasol, to the subject to affected areas of the skin once or twice daily for at least one day to about two weeks; wherein the said composition is substantially free of adverse effects and provides a similar or improved therapeutic effect as compared to that of the topical composition comprising highest approved topical dose of clobetasol i.e. TEMOVATE®. In some embodiments, low-dose clobetasol is about 0.025% (w/w) clobetasol. In some embodiments, low-dose clobetasol is about 0.025% (w/w) clobetasol propionate.

In some embodiments, the present invention relates to a method of treating psoriasis in a subject, the said method comprises a topical administration of a composition, comprising about 0.025% (w/w) of clobetasol, to the subject's affected areas of the skin; wherein the said composition is substantially free of adverse effects and provides a similar or improved therapeutic effect as compared to that of the topical composition comprising highest approved topical dose of clobetasol i.e. TEMOVATE®.

In some embodiments, the method of treating psoriasis involves topical administration of a composition comprising from about 0.005% to about 0.04% (w/w) of clobetasol, to the subject, once daily to the affected areas of the skin twice daily for a period of from about one day to two weeks to the affected areas of the skin for a period of from about one day to two weeks, or once daily to the affected areas of the skin for a period of from about one day to about four weeks or twice daily to the affected areas of the skin for a period of from about one day to about four weeks.

In some embodiments, the method of treating psoriasis involves topical administration of a composition comprising about 0.025% (w/w) clobetasol, to the subject, once daily to the affected areas of the skin twice daily for a period of about two weeks to the affected areas of the skin for a period of about two weeks, or once daily to the affected areas of the skin for a period of about four weeks or twice daily to the affected areas of the skin for a period of about four weeks. In some embodiments, the composition comprises about 0.025% (w/w) clobetasol propionate.

In some embodiments, the method of treating psoriasis involves topical administration of a composition comprising about 0.025% (w/w) of clobetasol to the subject, wherein the said subject having psoriatic lesions involving at least about 5% body surface area or from about 5% to about 10% body surface area or more than about 10% body surface area. In some embodiments, the composition is comprises about 0.025% (w/w) clobetasol propionate.

In some embodiments, the composition of the present invention is administered once or twice daily.

In some embodiments, the method of treating psoriasis in a subject, the said method comprises a topical administration of a composition comprising about 0.025% (w/w) of clobetasol propionate, to the subject once or twice daily to affected areas of the skin for about two weeks to about four weeks; wherein the said composition is substantially free of adverse effects and provides a similar or improved therapeutic effect as compared to that of the topical composition comprising highest approved topical dose of clobetasol i.e. TEMOVATE® and the said composition provides mean clobetasol propionate plasma levels less than about 130 pg/mL.

In some embodiments, the method of treating psoriasis in a subjects, the said method comprises a topical administration of a composition comprising about 0.025% (w/w) of clobetasol propionate, to the subject once or twice daily to affected areas of the skin for about two weeks to about four weeks; wherein the said composition is substantially free of adverse effects and provides a similar or improved therapeutic effect as compared to that of the topical composition comprising highest approved topical dose of clobetasol i.e. TEMOVATE® and the said composition provides post treatment mean clobetasol propionate plasma levels less than about 150 pg/mL.

In some embodiments, the method of treating psoriasis in a subject, the said method comprises a topical administration of a composition comprising about 0.025% (w/w) of clobetasol propionate, to the subject once or twice daily to affected areas of the skin for about two weeks to about four weeks; wherein the said composition is substantially free of adverse effects and provides a similar or improved therapeutic effect as compared to that of TEMOVATE® and the said composition provides post treatment mean clobetasol propionate plasma levels less than about 150 pg/mL.

In some embodiments, the method of treating psoriasis in a subject, the said method comprises a topical administration of a composition comprising about 0.025% (w/w) of clobetasol propionate, to the subject once or twice daily to affected areas of the skin for about two week to about four weeks; wherein the said composition is substantially free of adverse effects and provides a similar or improved therapeutic effect as compared to that of TEMOVATE® and the said composition provides post treatment mean clobetasol propionate plasma levels about from 130 pg/mL to 0 pg/ml.

In some embodiments, the method of treating psoriasis in a subject, the said method comprises a topical administration of a composition comprising about 0.025% (w/w) of clobetasol propionate, to the subject once or twice daily to affected areas of the skin for a period of from about two weeks to about four weeks; wherein the said composition is substantially free of adverse effects and provides a similar or improved therapeutic effect as compared to that of TEMOVATE® and the said composition provides post treatment mean clobetasol propionate plasma levels about from 150 pg/mL to 0 pg/ml.

In some embodiments, the method of treating psoriasis in a subjects, the said method comprises: topical administration of a composition comprising about 0.025% (w/w) of clobetasol propionate, to the subject once or twice daily to affected areas of the skin for a period of about two weeks; wherein the said composition is substantially free of adverse effects and provides a similar or improved therapeutic effect as compared to that of TEMOVATE® and the said composition provides post treatment mean clobetasol propionate plasma levels about from 150 pg/mL to 0 pg/ml.

In some embodiments, the present invention relates to a method of treating psoriasis in a subject having psoriatic lesions more than about 10% body surface area, the said method comprising topical administration of a composition, comprising about 0.025% (w/w) of clobetasol propionate, to the subject's affected areas of the skin twice daily for a treatment period of about four weeks; wherein the said method provides substantially free of adverse effects and provides a similar or improved therapeutic effect as compared to that of the topical composition comprising highest approved topical dose of clobetasol i.e. TEMOVATE®. In some embodiments, the topical administration of a composition comprising about 0.025% (w/w) clobetasol propionate, involves once or twice daily for a treatment period of four weeks. In some embodiments, the adverse effects are HPA axis suppression and/or reduction in DHEAS.

In some embodiments, the present invention provides a method of treating psoriasis in a subject, wherein the topical composition, comprising a low-dose clobetasol, is administered topically to the subject's affected skin area and said treatment provides a similar or an improved therapeutic effect and is substantially free of adverse effects as compared to that of TEMOVATE®. In some embodiments the composition is comprising about 0.025% (w/w) clobetasol. In some embodiments, the composition is comprising about 0.025% (w/w) clobetasol propionate.

In some embodiments, the present invention provides a method of treating psoriasis in a subject, wherein said topical composition, comprising about 0.025% of clobetasol, is administered topically to the subject's affected skin area and said treatment provides lower percentage of reduction in serum concentration of dehydroepiandrosterone sulfate (DHEAS) and has a similar or improved therapeutic effect as compared to that of TEMOVATE®. In some embodiments, the composition is comprises about 0.025% (w/w) clobetasol propionate.

In some embodiments, the present invention provides a method of treating psoriasis in a subject, wherein said topical composition, comprising about 0.025% (w/w) of clobetasol, is administered topically to the subject's affected skin area and said treatment provides lower percentage of reduction in serum concentration of dehydroepiandrosterone sulfate (DHEAS) and substantially free of HPA axis suppression; and has a similar or improved therapeutic effect as compared to that of TEMOVATE®. In some embodiments, the composition is comprises about 0.025% (w/w) clobetasol propionate.

In some embodiments, the present invention provides a method of treating a subject having psoriatic lesions more than about 10% of the body surface area, wherein the topical composition comprising low-dose clobetasol is administered to said subject's surface area and such treatment provides substantially no hypothalamic pituitary adrenal (HPA) axis suppression, lower percentage of reduction in serum concentration of dehydroepiandrosterone sulfate (DHEAS) with a similar or improved therapeutic effect as compared to that of TEMOVATE®. In some embodiments the composition is comprising about 0.025% (w/w) clobetasol. In some embodiments, the composition is comprising about 0.025% (w/w) clobetasol propionate.

In some embodiments, the present invention provides a method of treating psoriasis in a subject, wherein the topical composition, comprising low-dose clobetasol, is administered topically to the subject's affected skin area and said treatment provides a lower percentage of reduction in serum concentration of dehydroepiandrosterone sulfate (DHEAS) and low post treatment clobetasol mean plasma concentration in the subjects with no HPA axis suppression as compared to that of subjects with significant HPA axis suppression.

In some embodiments, the present invention provides a method of treating psoriasis in a subject, wherein the topical composition, comprising about 0.025% (w/w) clobetasol propionate, is administered topically to the subject's affected skin area and said treatment provides a lower percentage of reduction in serum concentration of dehydroepiandrosterone sulfate (DHEAS) and low post treatment clobetasol propionate mean plasma concentration in the subjects with no HPA axis suppression as compared to that of subjects with significant HPA axis suppression.

In some embodiments, the present invention provides a method of treating psoriasis in a subject, wherein the topical composition, comprising low-dose clobetasol, is administered topically to the subject's affected skin area and said treatment provides a lower percentage of reduction in serum concentration of dehydroepiandrosterone sulfate (DHEAS) and low post treatment clobetasol mean plasma concentration in the subjects with significantly no HPA axis suppression as compared to that of subjects with significant HPA axis suppression.

In some embodiments, the present invention provides a method of treating psoriasis in a subject, wherein the topical composition, comprising about 0.025% (w/w) clobetasol, is administered topically to the subject's affected skin area once or twice daily for a period of at least one day to about four weeks; and said treatment provides lower percentage of reduction in serum concentration of dehydroepiandrosterone sulfate (DHEAS) and low post treatment clobetasol plasma concentration in the subjects with significantly no HPA axis suppression as compared to that of subjects with significant HPA axis suppression.

In some embodiments, the present invention provides a method of treating psoriasis in a subject, wherein the topical composition, comprising about 0.025% (w/w) clobetasol propionate, is administered topically to the subject's affected skin area for a period of at least one day to about four weeks; and said treatment provides lower percentage of reduction in serum concentration of dehydroepiandrosterone sulfate (DHEAS) and low post treatment clobetasol propionate plasma concentration in the subjects with significantly no HPA axis suppression as compared to that of subjects with significant HPA axis suppression.

In some embodiments, the present invention provides a method of treating psoriasis in a subject, wherein the topical composition, comprising about 0.025% (w/w) clobetasol, is administered topically to the subject's affected skin area for a period of at least one day to about two weeks; and said treatment provides lower percentage of reduction in serum concentration of dehydroepiandrosterone sulfate (DHEAS) and low post treatment clobetasol plasma concentration in the subjects with no HPA axis suppression as compared to that of subjects with significant HPA axis suppression.

In some embodiments, the present invention provides a method of treating psoriasis in a subject, wherein the topical composition, comprising about 0.025% (w/w) clobetasol propionate, is administered topically to the subject's affected skin area for a period of at least one day to about two weeks; and said treatment provides lower percentage of reduction in serum concentration of dehydroepiandrosterone sulfate (DHEAS) and low post treatment clobetasol propionate plasma concentration in the subjects with no HPA axis suppression as compared to that of subjects with significant HPA axis suppression.

In some embodiments, the present invention provides a method of treating psoriasis in a subject, wherein the topical composition, comprising about 0.025% (w/w) of clobetasol propionate, is administered topically to the subject's affected skin area, wherein the said method provides post treatment mean clobetasol propionate plasma concentration is significantly lower than that of TEMOVATE®. In some embodiments, the post treatment mean clobetasol propionate plasma levels are less than about 150 pg/ml or the post treatment mean clobetasol propionate plasma levels are less than about 130 pg/ml, or the post treatment mean clobetasol propionate plasma levels are less than about 100 pg/ml or the post treatment mean clobetasol propionate plasma levels are less than about 75 pg/ml.

In some embodiments, the present invention provides a method of treating psoriasis in a subject, wherein the topical composition, comprising from about 0.025% (w/w) clobetasol propionate, is administered topically to the subject's affected skin area, wherein the said method provides post treatment mean clobetasol propionate plasma concentration is significantly lower than that of TEMOVATE®. In some embodiments, the post treatment mean clobetasol propionate plasma levels are less than about 150 pg/ml or the post treatment mean clobetasol propionate plasma levels are less than about 130 pg/ml, or the post treatment mean clobetasol propionate plasma levels are less than about 100 pg/ml or the post treatment mean clobetasol propionate plasma levels are less than about 75 pg/ml or the post treatment mean clobetasol propionate plasma levels are less than about 50 pg/ml or the post treatment mean clobetasol propionate plasma levels are less than about 25 pg/ml or the post treatment mean clobetasol propionate plasma levels are below quantifiable level.

In another aspect of the present invention, psoriasis is mild to moderate plaque psoriasis In another aspect of the present invention, psoriasis is moderate to severe plaque psoriasis.

In some embodiments, the present invention provides the post treatment mean clobetasol propionate plasma levels are significantly less in the subjects having no HPA axis suppression as compared to that of subjects with HPA axis suppression.

In some embodiments, the method of treating psoriasis in a subject, involves the subject is having psoriatic lesions at least about 5% of the body surface area or the subject is having psoriatic lesions about 5% to about 10% of the body surface area or the subject is having psoriatic lesions more than about 10% of the body surface area.

An aspect of the present invention relates to method of administering a topical composition comprising about 0.025% (w/w) clobetasol for the treatment of psoriasis. The composition is administered twice daily for a period of about two weeks, or the composition is administered once daily for a period of about two weeks or the composition is administered once daily for a period of about four weeks or the composition is administered twice daily for a period of about four weeks.

An aspect of the present invention relates to method of administering a topical composition comprising about 0.025% (w/w) clobetasol propionate for the treatment of psoriasis. The composition is administered twice daily for a period of about two weeks, or the composition is administered once daily for a period of about two weeks or the composition is administered once daily for a period of about four weeks or the composition is administered twice daily for a period of about four weeks.

In some embodiments, the composition of the present invention provides significantly greater percent reduction in serum DHEAS concentration and a significantly greater mean post-treatment clobetasol propionate plasma concentration in subjects HPA axis suppression than subjects without HPA axis suppression.

In another embodiment, a topical composition comprising about 0.025% w/w clobetasol, in which the percentage reduction in serum concentration of dehydroepiandrosterone sulfate (DHEAS) in subjects with HPA axis suppression was significantly greater than in subjects without HPA axis suppression In some embodiments, method of treating psoriasis, wherein the topical composition of the present invention comprises about 0.025% (w/w) clobetasol and can be administered more than about 2 grams/day with substantially free of HPA axis suppression.

In some embodiments, method of treating psoriasis, wherein the topical composition of the present invention comprises about 0.025% (w/w) clobetasol propionate and can be administered more than about 2 grams/day with substantially free of HPA axis suppression.

In some embodiments, method of treating psoriasis, wherein the topical composition of the present invention comprises about 0.025% (w/w) clobetasol and can be administered more than about 2 grams/day with lower percentage reduction of serum concentration of DHEAS.

In some embodiments, method of treating psoriasis, wherein the topical composition of the present invention comprises about 0.025% (w/w) clobetasol propionate and can be administered more than about 2 grams/day with lower percentage reduction of serum concentration of DHEAS.

In some embodiments, method of treating eczema, wherein the topical composition of the present invention comprises about 0.025% (w/w) clobetasol and can be administered more than about 2 grams/day with lower percentage reduction of serum concentration of DHEAS.

In some embodiments, method of treating eczema, wherein the topical composition of the present invention comprises about 0.025% (w/w) clobetasol propionate and can be administered more than about 2 grams/day with lower percentage reduction of serum concentration of DHEAS.

In some embodiments, the method comprises administering topical composition, comprising about 0.025% (w/w) clobetasol, once or twice daily with the dose of from about 1 gram to about 12 grams per day for a period of about one day to about two weeks. In another aspect, the composition is comprising about 0.025% (w/w) of clobetasol propionate.

In some embodiments, the method comprises administering a topical composition, comprising about 0.025% (w/w) clobetasol, once or twice daily with the dose of from about 0.1 mg to 3.15 mg per day of clobetasol for a period of about two weeks. In another aspect, clobetasol is clobetasol propionate In some embodiments, the method comprises administering topical composition, comprising about 0.025% (w/w) clobetasol, once or twice daily with the dose of from about 0.25 mg to 2.5 mg per day of clobetasol for a period of about two weeks. In another aspect, clobetasol is clobetasol propionate In some embodiments, the method comprises administering topical composition, comprising about 0.025% (w/w) clobetasol, once or twice daily with the dose of from about 0.25 mg to 2.5 mg per day of clobetasol for a period of about two weeks. In another aspect, clobetasol is clobetasol propionate In some embodiments, the topical composition of the present invention can be administered more than about 2 grams/day, but not exceeding about 12 g/day for one week in the subject with eczema.

In some embodiments, the topical composition of the present invention can be administered more than about 60 g/week without causing clinically significant HPA axis suppression in the subject.

In some embodiments, the present invention relates to a method of treating psoriasis in a subject, the said method comprises administering topical composition, comprising about 0.025% (w/w) of clobetasol, once or twice daily with a dose of from about 1 grams to about 7 grams per day of said topical composition for a period of about two weeks; wherein the said method administers clobetasol from about 0.25 mg to about 2.5 mg per day; and provides substantially free of HPA axis suppression and provides a similar or improved therapeutic effect as compared to that of the topical composition comprising highest approved topical dose of clobetasol i.e. TEMOVATE® and the said composition provides mean clobetasol plasma levels less than about 130 pg/mL. In another aspect, clobetasol is clobetasol propionate.

In some embodiments, the present invention relates to a method of treating psoriasis in a subject, the said method comprises administering topical composition, comprising about 0.025% (w/w) of clobetasol, once or twice daily with a dose of from about 1 grams to about 7 grams per day of said topical composition for a period of about two weeks; wherein the said method administers clobetasol from about 0.25 mg to about 2.5 mg per day; and provides lower percentage reduction of serum concentration of DHEAS and provides a similar or improved therapeutic effect as compared to that of the topical composition comprising highest approved topical dose of clobetasol i.e. TEMOVATE® and the said composition provides mean clobetasol plasma levels less than about 130 pg/mL. In another aspect, clobetasol is clobetasol propionate.

In some embodiments, the present invention relates to a method of treating psoriasis in a subject, the said method comprises administering topical composition, comprising about 0.025% (w/w) of clobetasol, once or twice daily with the a dose of from about 1 grams to about 7 grams per day of said topical composition for a period of two weeks; wherein the said method administers clobetasol from about 0.25 mg to about 2.25 mg per day; and the said method provides substantially free of adverse effects and provides a similar or improved therapeutic effect of highest approved topical dose of clobetasol i.e. TEMOVATE®. In some embodiments, the said method is treating psoriasis in a subjects having psoriatic lesions at least about 5% body surface area or treating psoriasis in a subjects having psoriatic lesions from about 5% to about 10% body surface area or treating psoriasis in a subjects having psoriatic lesions more than about 10% body surface area. In another aspect, clobetasol is clobetasol propionate.

In some embodiments, the topical composition of the present invention provides mean clobetasol plasma levels in the subjects, which is about 1 fold less than the levels of topical composition comprising highest approved topical dose of clobetasol i.e. 0.05% (w/w) or about 1.5 folds less than the levels of topical composition comprising highest approved topical dose of clobetasol i.e. 0.05% (w/w) or about 2.5 folds less than the levels of topical composition comprising highest approved topical dose of clobetasol i.e. 0.05% (w/w) or about 3.0 folds less than the levels of topical composition comprising highest approved topical dose of clobetasol i.e. 0.05% (w/w) or about 3.5 folds less than the levels of topical composition comprising highest approved topical dose of clobetasol i.e. 0.05% (w/w) clobetasol with a similar or improved therapeutic efficacy.

In some embodiments, the therapeutic efficacy of the topical composition of the present invention is equivalent or improved when compared to that of the highest approved topical dose of clobetasol i.e. TEMOVATE®. In some embodiments, at least 30% of the subject treated with the topical composition of the present invention from severe or very severe, moderate to severe, or moderate to mild, minimal or almost clear or clear condition in the 15 days treatment.

In some embodiments, the topical composition of the present invention forms a depot on the skin forming an occlusive film, thereby extending the duration of active agent action while allowing "breathing" of the skin.

In some embodiment, the compositions of the present invention may have pH values ranging from about 3.0 to about 7.0 or from about 3.5 to about 6.0.

The compositions of the present invention can be dispensed in any dispensing device such as laminated tubes or lacquered aluminum tubes. Laminated tubes contains propylene glycol-free topical compositions, wherein the device is a lamitube comprised of 5 layers White PE, Ethylene acrylic acid (EAA), Aluminum foil, EAA, Virgin natural PE such that the composition is consistently discharge on application. Used. In an embodiment, the compositions of the present invention are dispensed in lacquered aluminum tubes which are very useful and very effective in storing the cream.

The present invention is illustrated below by reference to the following examples. However, one skilled in the art will appreciate that the specific methods and results discussed are merely illustrative of the present invention, and not to be construed as limiting the application. The following examples may include compilations of data that are representative of data gathered at various times during the course of development and experimentation related to the present invention.

EXAMPLES

The following general manufacturing processes were followed to prepare Examples 1-7:

Manufacturing Process I:

a) preparing an oil phase by melting and stirring stearyl alcohol, cetyl alcohol; glyceryl stearate and PEG 100 stearate and lanolin followed by methyl paraben and propyl paraben, and mineral oil, b) preparing an aqueous phase by adding sorbitol solution into heated purified water, c) preparing an emulsion by adding the oil phase of step (i) to the aqueous phase (ii) or vice versa under homogenization, d) dissolving a premixed solution of clobetasol propionate in a diethylene glycol monoethyl ether and the followed by addition of BHT and homogenized to obtain a clobetasol propionate solution, e) adding the clobetasol propionate solution obtained in step (iv) to the emulsion prepared in step (iii) followed by homogenization to obtain a cream composition.

Manufacturing Process II:

a) preparing an oil phase by melting and stirring cetostearyl alcohol; whitewax; glyceryl stearate and PEG 100 stearate and isopropyl myristate followed by methyl paraben and propyl paraben, and cyclomethicone, b) preparing an aqueous phase by heating the purified water, c) preparing an emulsion by adding the oil phase of step (i) to the aqueous phase (ii) or vice versa under homogenization, d) dissolving a premixed solution of clobetasol propionate in a diethylene glycol monoethyl ether and the followed by addition of BHT and homogenized to obtain a clobetasol propionate solution, e) adding the clobetasol propionate solution obtained in step (iv) to the emulsion prepared in step (iii) followed by homogenization to obtain a cream composition.

Example 1: Clobetasol Propionate (0.05% (w/w)) Cream

A composition of the present example was prepared by following Manufacturing Process-I using the following ingredient amounts.

| Ingredient | Percentage (w/w) |
| --- | --- |
| Clobetasol propionate | 0.05 |
| Stearyl alcohol | 2 |
| Cetyl alcohol | 2 |
| Glyceryl stearate & PEG 100 | 7.5 |
| Lanolin | 2 |
| Mineral oil | 5 |
| Sorbitol solution, 70% | 2 |
| Diethylene glycol monoethyl ether | 3 |
| Butylated hydroxy toluene | 0.05 |
| Methyl paraben | 0.2 |
| Propyl paraben | 0.4 |
| Purified water | q.s to 100 |

Example 2: Clobetasol Propionate (0.025% (w/w)) Cream

A composition of the present example was prepared by following Manufacturing Process-I using the following ingredient amounts.

| Ingredient | Percentage (w/w) |
| --- | --- |
| Clobetasol propionate | 0.025 |
| Stearyl alcohol | 2 |
| Cetyl alcohol | 2 |
| Glyceryl stearate & PEG 100 stearate | 7.5 |
| Lanolin | 2 |
| Mineral oil | 5 |
| Sorbitol solution, 70% | 2 |
| Diethylene glycol monoethyl ether | 10 |
| Butylated hydroxy toluene | 0.05 |
| Methyl paraben | 0.2 |
| Propyl paraben | 0.4 |
| Purified water | q.s to 100 |

Example 3: Clobetasol Propionate (0.025% (w/w)) Cream

A composition of the present example was prepared by following Manufacturing Process-I using the following ingredient amounts.

| Ingredient | Percentage (w/w) |
| --- | --- |
| Clobetasol propionate | 0.025 |
| Stearyl alcohol | 2 |
| Cetyl alcohol | 2 |
| Glyceryl stearate & PEG 100 stearate | 7.5 |
| Lanolin | 2 |
| Mineral oil | 5 |
| Sorbitol solution, 70% | 2 |
| Diethylene glycol monoethyl ether | 3 |
| Butylated hydroxy toluene | 0.05 |
| Methyl paraben | 0.2 |
| Propyl paraben | 0.4 |
| Purified water | q.s to 100 |

Example 4: Clobetasol Propionate (0.025% (w/w)) Cream

A composition of the present example was prepared by following Manufacturing Process-I using the following ingredient amounts.

| Ingredient | Percentage (w/w) |
| --- | --- |
| Clobetasol propionate | 0.025 |
| Stearyl alcohol | 1.5 |

-continued

| Ingredient | Percentage (w/w) |
| --- | --- |
| Cetyl alcohol | 2.5 |
| Glyceryl stearate & PEG 100 stearate | 7.5 |
| Lanolin | 3 |
| Mineral oil | 4 |
| Sorbitol solution, 70% | 2 |
| Diethylene glycol monoethyl ether | 5 |
| Butylated hydroxy toluene | 0.05 |
| Methyl paraben | 0.2 |
| Propyl paraben | 0.4 |
| Purified water | q.s to 100 |

Example 5: Clobetasol Propionate (0.025% (w/w)) Cream

A composition of the present example was prepared by following Manufacturing Process-II using the following ingredient amounts.

| Ingredient | Percentage (w/w) |
| --- | --- |
| Clobetasol propionate | 0.025 |
| Cetostearyl alcohol | 3 |
| Glyceryl stearate & PEG 100 stearate | 6 |
| White wax | 1 |
| Diethylene glycol monoethyl ether | 3 |
| Butylated hydroxy toluene | 0.05 |
| Isopropyl myristate | 10 |
| Cyclomethicone | 5 |
| Methyl paraben | 0.2 |
| Propyl paraben | 0.4 |
| Purified water | q.s to 100 |

Example 6: Clobetasol Propionate (0.025% (w/w)) Cream

A composition of the present example was prepared by following Manufacturing Process-II using the following ingredient amounts.

| Ingredient | Percentage (w/w) |
| --- | --- |
| Clobetasol propionate | 0.025 |
| Cetostearyl alcohol | 3 |
| Glyceryl stearate & PEG 100 stearate | 6 |
| White wax | 1 |
| Diethylene glycol monoethyl ether | 10 |
| Butylated hydroxy toluene | 0.05 |
| Isopropyl myristate | 10 |
| Cyclomethicone | 5 |
| Methyl paraben | 0.2 |
| Propyl paraben | 0.4 |
| Purified water | q.s to 100 |

Example 7: Clobetasol Propionate (0.05% (w/w)) Cream

A composition of the present example was prepared by following Manufacturing Process-II using the following ingredient amounts.

| Ingredient | Percentage (w/w) |
| --- | --- |
| Clobetasol propionate | 0.05 |
| Cetostearyl alcohol | 3 |

-continued

| Ingredient | Percentage (w/w) |
| --- | --- |
| Glyceryl stearate & PEG 100 stearate | 6 |
| White wax | 1 |
| Diethylene glycol monoethyl ether | 10 |
| Butylated hydroxy toluene | 0.05 |
| Isopropyl myristate | 10 |
| Cyclomethicone | 5 |
| Methyl paraben | 0.2 |
| Propyl paraben | 0.4 |
| Purified water | q.s to 100 |

Example 8

Physical and Chemical stability evaluation of the topical compositions of the present invention: All the compositions were evaluated for the physical changes such as color during the studies and all the compositions were remained in the off white to white cream throughout the study and did not show any significant changes.

The prepared formulation of example 1, example 2, example 3, and example 6 were filled into closed container and exposed to the various stability testing conditions such as 25° C. and 60% relative humidity (RH), 30° C. and 65% RH, and 40° C. and 75% RH for twelve months, and analyses at various storage points are shown in Tables.

TABLE 1

| Specification | Assay | Related compound A | Highest single unknown impurity | % Total impurities |
| --- | --- | --- | --- | --- |
| Example 1 | | | | |
| Initial | 98.2 | ND | ND | 0.0 |
| 1 M 30° C./65% RH | 100.7 | ND | ND | 0.0 |
| 1 M 40° C./75% RH | 100.7 | ND | ND | 0.0 |
| 2 M 25° C./60% RH | 100.4 | ND | ND | 0.0 |
| 2 M 40° C./75% RH | 99.4 | ND | ND | 0.0 |
| 3 M 25° C./60% RH | 99.6 | ND | ND | 0.0 |
| 3 M 30° C./65% RH | 98.6 | ND | ND | 0.0 |
| 3 M 40° C./75% RH | 99.0 | ND | ND | 0.0 |
| Example 2 | | | | |
| Initial | 102.0 | ND | ND | 0.0 |
| 1 M 30° C./65% RH | 100.3 | ND | ND | 0.0 |
| 1 M 40° C./75% RH | 100.1 | ND | ND | 0.0 |
| 2 M 30° C./65% RH | 98.9 | ND | ND | 0.0 |
| 2 M 40° C./75% RH | 98.7 | ND | ND | 0.0 |
| 3 M 25° C./60% RH | 97.1 | ND | ND | 0.0 |
| 3 M 30° C./65% RH | 97.1 | ND | ND | 0.0 |
| 3 M 40° C./75% RH | 96.3 | ND | ND | 0.0 |
| Example 3 | | | | |
| Initial | 101.8 | ND | 0.14 | 0.19 |
| 1 M 25° C./60% RH | 103.3 | ND | 0.10 | 0.27 |
| 1 M 30° C./65% RH | 100.8 | ND | 0.09 | 0.19 |

TABLE 1-continued

| Specification | Assay | Related compound A | Highest single unknown impurity | % Total impurities |
|---|---|---|---|---|
| 1 M 40° C./75% RH | 100.4 | ND | 0.11 | 0.30 |
| 2 M 30° C./65% RH | 99.2 | ND | 0.182 | 0.309 |
| 2 M 40° C./75% RH | 99.0 | ND | 0.193 | 0.404 |
| 3 M 25° C./60% RH | 104.9 | ND | 0.17 | 0.40 |
| 3 M 30° C./65% RH | 102.4 | ND | 0.17 | 0.46 |
| Example 6 | | | | |
| Initial | 102.9 | ND | ND | 0.0 |
| 1 M 30° C./65% RH | 101.9 | ND | ND | 0.0 |
| 1 M 40° C./75% RH | 101.3 | ND | ND | 0.0 |
| 2 M 30° C./65% RH | 102.3 | ND | ND | 0.0 |
| 2 M 40° C./75% RH | 101.1 | ND | ND | 0.0 |
| 3 M 30° C./65% RH | 98.3 | ND | ND | 0.0 |
| 3 M 40° C./75% RH | 99.5 | ND | ND | 0.0 |
| 6 M 25° C./60% RH | 99.9 | — | ND | ND |
| 6 M 30° C./65% RH | 99.1 | — | ND | ND |
| 6 M 40° C./75% RH | 98.4 | — | ND | ND |
| 12 M 2-8° C. | 100.5 | — | 0.10 | 0.17 |
| 12 M 25° C./60% RH | 101.1 | — | 0.10 | 0.22 |
| 12 M 30° C./65% RH | 100.9 | — | 0.21 | 0.21 |

Example 9: In Vitro Dissolution Study

Figure 2:
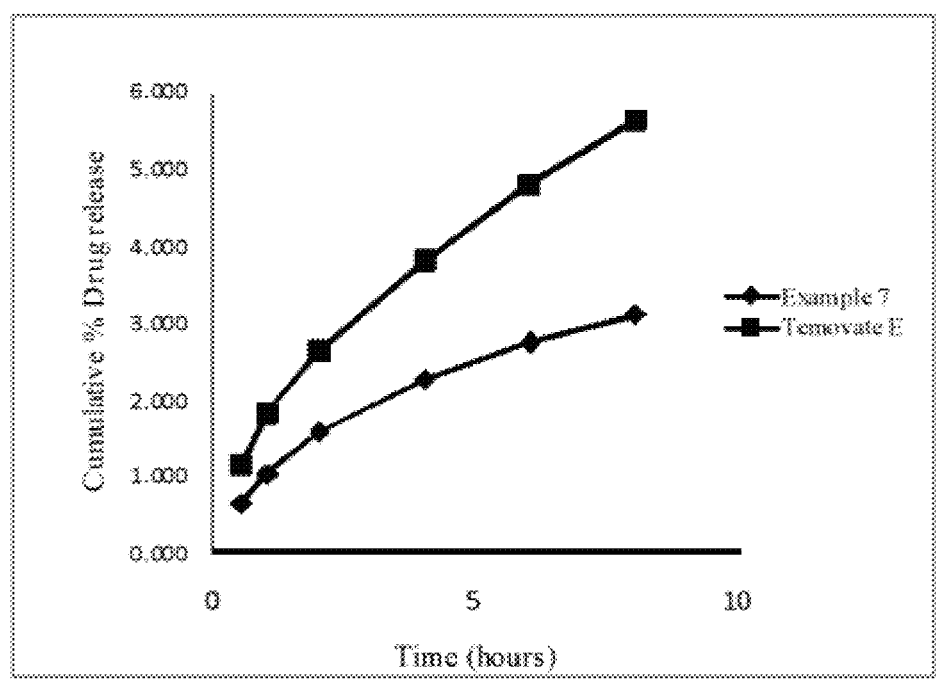
FIG. 2 shows drug release for a composition of the invention and a commercially available product.

Comparative in vitro dissolution profile testing, showing drug release from Example 3 and Example 7 Vs. TEMOVATE E® cream, was conducted. The cumulative percentage of drug released is shown in FIGS. 1 and 2 in comparison with TEMOVATE E® cream. The test was conducted as described below:

A Franz diffusion cell was fitted with a 0.45 μm nylon membrane clamped between the donor and receptor compartments. The receptor media was a mixture of water and acetone (35:65 by volume) with a replacement volume of 11.0 mL, a sampling volume of 2.0 mL was drawn at 30 min, 1, 2, 4, 6, and 8 hours respectively, and the temperature was maintained at 32±0.5° C. About 200 mg of the formulation was applied uniformly over the membrane. The donor compartment was covered using PARAFILM® (hydrocarbon wax and polyolefin blend). Receptor fluid was analyzed for the drug, using high performance liquid chromatography (HPLC).

Example 10: In Vivo Efficacy Study

The UV erythema test is a suitable and accepted procedure for standardized comparison of anti-inflammatory action of topical medications. In order to allow precise determination of the UV doses, individual sensitivity to UV were determined followed by performance of a light scale to determine the minimal erythemal dose (MED).

UV exposure was performed using 1.5 MED, with less than 30 cm² skin surface was irradiated. The pharmaceutical compositions given in the examples and TEMOVATE E® cream were applied at the dose approximately 10 mg/cm² over the UV exposed skin surface. The assessment of erythema suppression will be determined by chromametric measurement.

Figure 3:
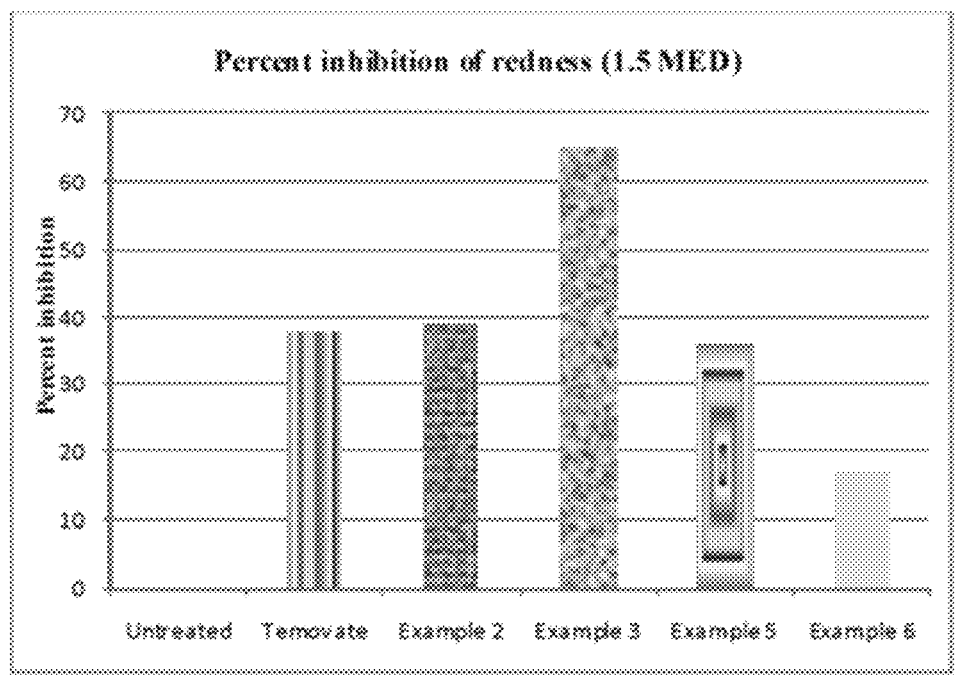
FIG. 3 shows percent of inhibition of redness for an untreated control, compositions of the invention, and a commercially available product.
Figure 4:
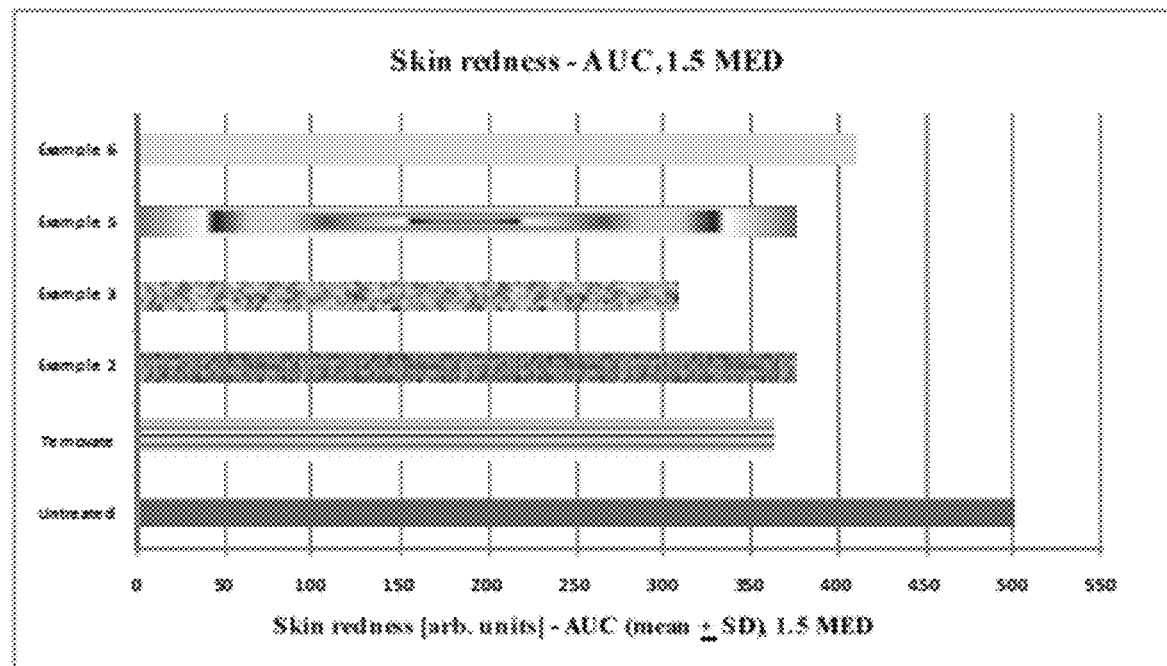
FIG. 4 shows and AUC of skin redness for an untreated control, compositions of the invention, and a commercially available product.
Figure 5:
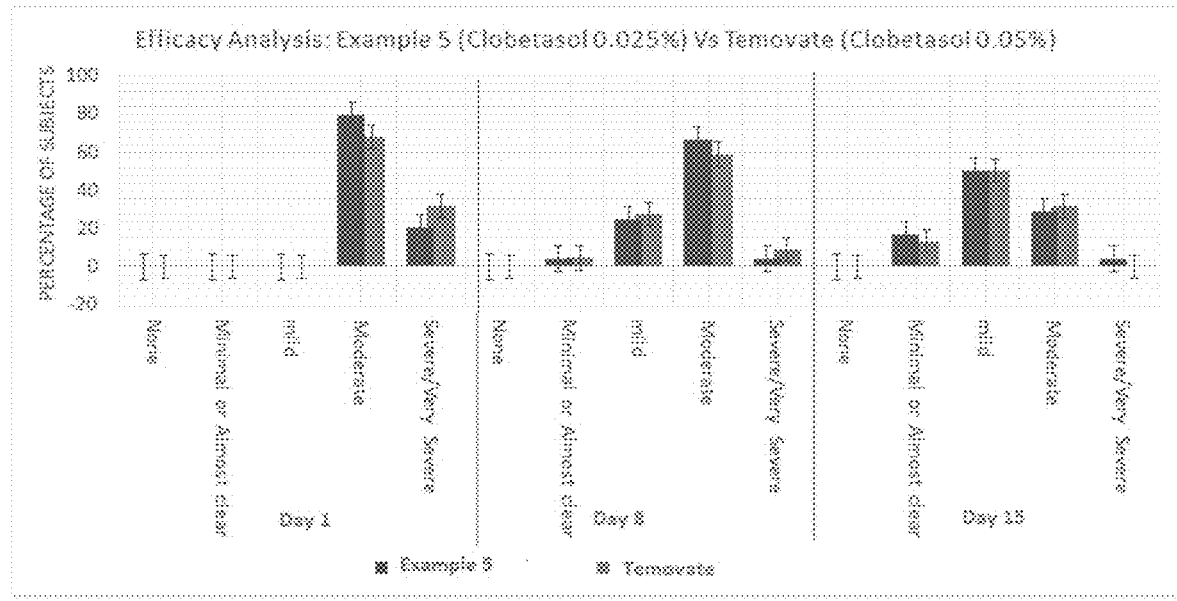
FIG. 5 shows efficacy analysis: Investigator's Global Assessment (IGA)—Example 5 Vs TEMOVATE® Cream.
Figure 6:
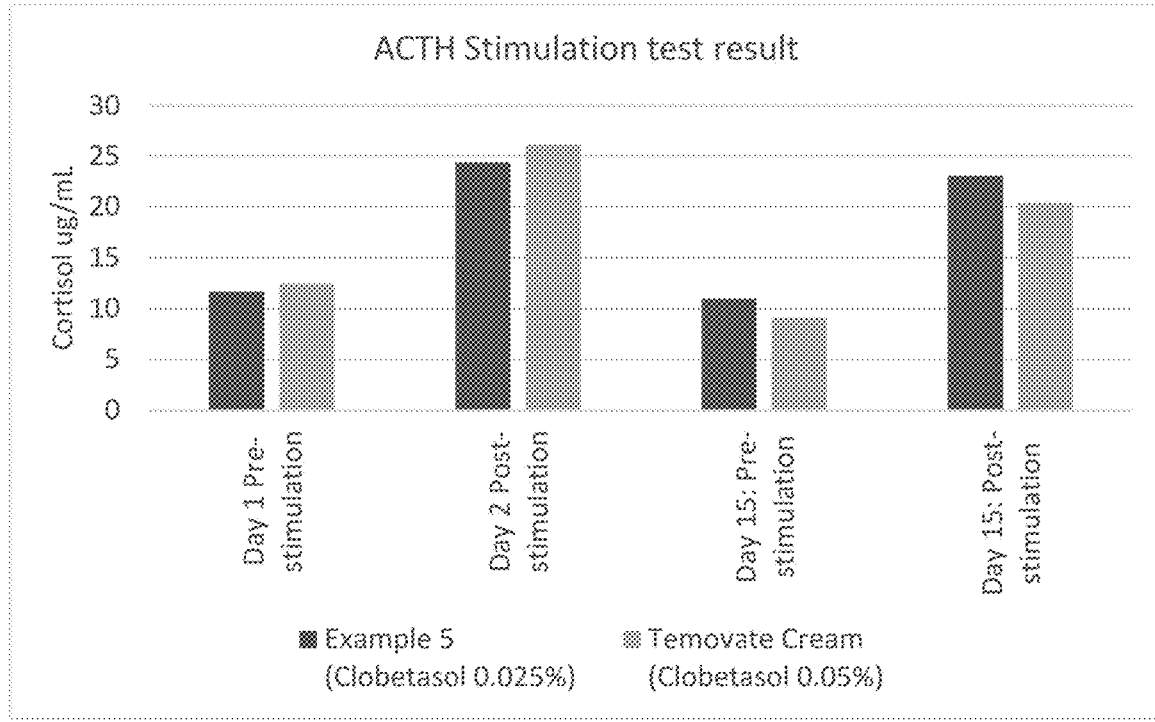
FIG. 6 shows ACTH Stimulation Test Result (Serum Cortisol levels in ug/dL).
Figure 7:
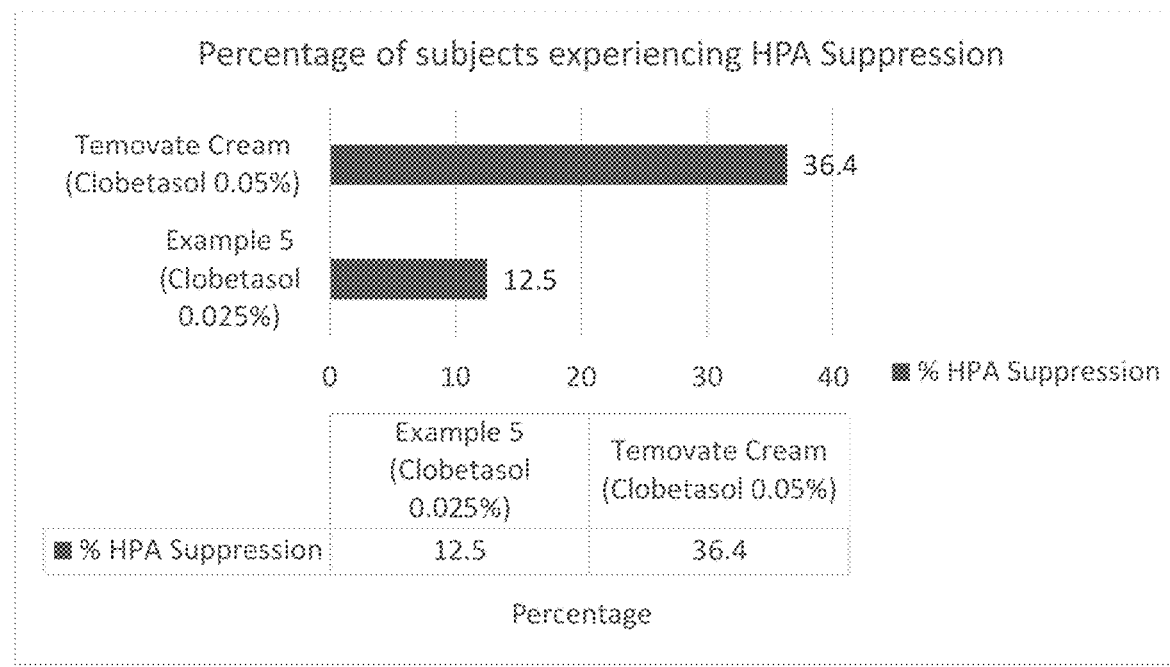
FIG. 7 shows results of HPA axis suppression (ACTH stimulation test).
Figure 8:
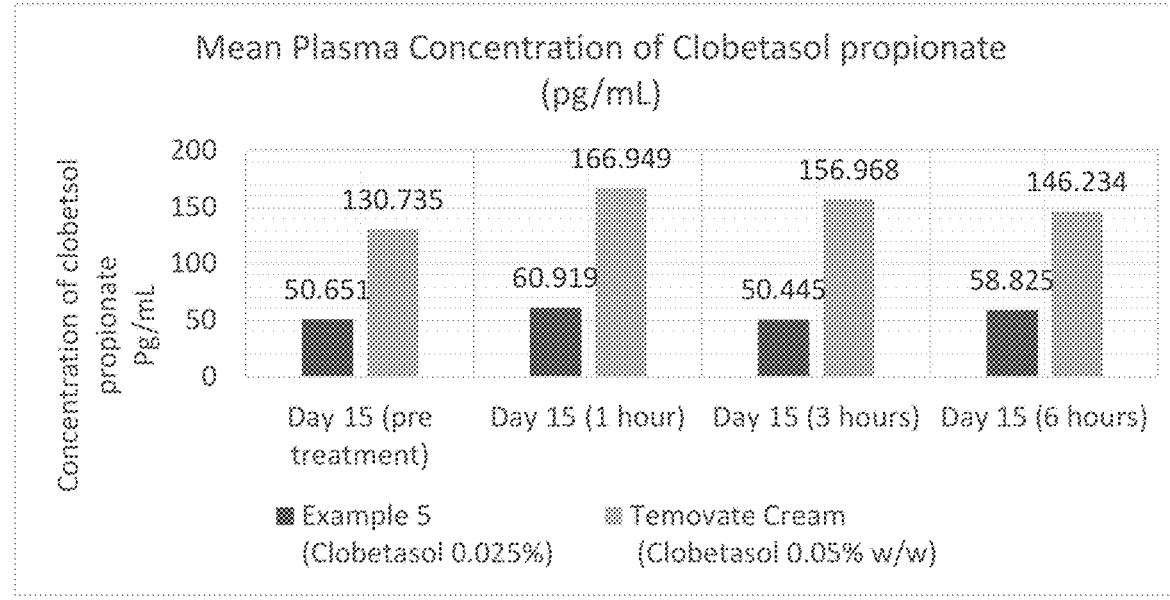
FIG. 8 shows mean plasma concentration of clobetasol propionate: Example 5 Vs TEMOVATE® Cream.

The percent of inhibition of redness and AUC in comparison with TEMOVATE E® cream is shown in FIGS. 3 and 4, respectively.

While several particular forms of the application have been illustrated and described, it will be apparent that various modifications and combinations of the application detailed in the text can be made without departing from the spirit and scope of the application.

Example 11: Effect on Endocrine Systems (Hypothalamic-Pituitary-Adrenal Axis Suppression Study)

Methods: This was 15 days, randomized, multicentre, multi-dose, comparator controlled, open label study, and the subjects were above 18 years old with moderate to severe plaque psoriasis and they were randamized to treatment with either Example 5 Cream or TEMOVATE® cream in a 1:1 ratio. These investigational products were applied twice daily to all affected areas on the body excluding face, scalp, groin, axillae and other intertriginous areas. The subjects had 20 to 50% BSA treated to achieve maximal use exposure. The subjects were visited Screening, Baseline (Day 1), Day 8, Day 15 and Day 43 (if needed to confirm recovery). Clinical determinations of disease severity was conducted using the Investigator Global Assessment (IGA) for overall severity at each visit. Subjects were tested for HPA axis function using the ACTH stimulation test (i.e., a cosyntropin i.v. or i.m. injection) at the Screening Visit (at least 14 days and no more than 28 days prior to Baseline) and at Day 15. In addition, blood samples for serum dehydroepiandrosterone sulfate (DHEAS) was taken at Screening, on Day 8 and at the time of the ACTH stimulation test on Day 15 (pre-test sample) as a secondary measure of HPA axis suppression. At the time of the screening ACTH stimulation test, a PK blood sample was taken to obtain a baseline value (PK screening sample). On Day 15, subjects were applied the last dose of study product at the clinic up to 60 minutes after a pre-treatment PK blood sample was taken (0 hour-Day 15). PK blood samples was then collected at 1, 3 and 6 hours (±5 minutes) after application of the study product.

Treatment regimen: Subjects were administered study product (Example 5), twice daily with approximately 12 hours between applications for 15 days starting on Day 1 during the study visit. Subjects had applied study product to all affected areas except the face, scalp, groin, axillae and other intertriginous areas. The target dose was at least 5 to 7 g per day (1 teaspoon of cream, twice daily, applied at approximately 1 mg/cm2 on 20% BSA—3000 cm2). All baseline affected areas and newly affected areas have been treated until the end of the study even if cleared. The investigator had marked the affected areas (in the source document), updated the marking at each visit, and reminded the subjects where study product was to be applied at each visit using the marking. Study product have been applied directly onto affected areas and rubbed in gently and completely. Study product have been applied after bathing, if applicable.

The changes in IGA score were evaluated on Day 1, Day 8, and Day 15. The change in IGA score from 4 to 0-1 was considered success in the treatment as depicted below:

| Score | Grade | Definition |
|---|---|---|
| 0 | None | No plaque elevation above normal skin level |
| | | may have residual non-erythematous discoloration |
| | | no psoriatic scale |
| | | no erythema |
| 1 | Minimal or Almost clear | No more than: |
| | | very slight elevation above normal skin level |
| | | faint light pink coloration |
| | | occasional very fine scale partially covering some of the lesions |
| 2 | Mild | No more than: |
| | | slight but definite elevation of plaque above normal skin level |
| | | light red coloration |
| | | fine scale with some lesions partially covered |
| 3 | Moderate | No more than: |
| | | definite elevation with rounded or sloped edges to plaque |
| | | definite red coloration |
| | | somewhat coarse scale with most lesions partially covered |
| 4 | Severe/Very Severe | At least one: |
| | | marked elevation with hard, sharp edges to plaque |
| | | dark red coloration |
| | | coarse, thick scale with virtually all lesions mostly covered and a rough surface |

ACTH Stimulation Test

The subjects were tested for HPA axis function using the ACTH stimulation test (cosyntropin i.v. or i.m. injection) at a screening visit and at Day 15 visit. If HPA axis was suppressed at the Day 15 visit, another test had been administered 28 days later (at approximately Day 43) to confirm recovery. The ACTH stimulation test were repeated approximately every 28 days until recovery is confirmed (or until the cause of suppression is diagnosed). The test should be conducted between the hours of 7:00 and 9:30 AM. The Screening Visit test must be normal to be eligible for the study (cortisol level >18 ug/dL at 30 minutes post stimulation). The Day 15 test should be performed within 1 hour of the time when the Screening Visit test was performed.

Serum DHEAS. Blood samples for serum DHEAS was taken at the time of the screening ACTH stimulation test, on Day 8 and at the time of the ACTH stimulation test on Day 15 (pre-test sample) as a secondary measure of HPA axis suppression.

It is observed that no significant HPA axis suppression was noted with Example 5 composition. The results of the HPA suppression study showed a much lower potential for this adverse effect compared to TEMOVATE® (clobetasol propionate) Cream, 0.05% (w/w). With regard to therapeutic efficacy, Example 5 and TEMOVATE® were similar or almost identical in efficacy (IGA score), and with regard to HPA axis suppression, Example 5 did not show clinically significant HPA axis suppression when compared to that of TEMOVATE® cream.

CONCLUSION

In summary, at the end of 15 days treatment with composition of Example 5, about 50% of subjects were converted to "mild" and about 16.7% to "minimal or almost clear condition" from "moderate, severe/very severe conditions" as compared to 15 days treatment with TEMOVATE® cream wherein about 50% of subjects were converted to "mild" and 13.6% to "minimal or almost clear condition from moderate, severe/very severe conditions".

Based on efficacy assessment as described in Table 2 (Example 5—clobetasol 0.025% (w/w) cream and TEMOVATE® Cream—0.05% (w/w)), both the compositions had shown similar or almost identical therapeutic efficacy.

With regard to the results of HPA axis suppression (Table 3 and Table 4), composition of the present invention (Example 5) had shown about 12.5% of the total subjects had HPA suppression i.e. 3 subjects out of 24 had HPA axis suppression, whereas TEMOVATE® cream had shown about 36.4% of the total subjects had HPA axis suppression i.e. 8 subjects out of 22 had HPA axis suppression. The mean plasma levels of clobetasol for TEMOVATE® was around 2.5 times more than that of Example 5, confirming the much lower systemic exposure by Example 5 composition and the average post-treatment plasma levels of clobetasol was significantly lower for the Example 5 composition (Table 7).

The subjects with HPA axis suppression had about more than 3 times mean plasma clobetasol levels of those without HPA axis suppression which validated that the higher exposure leads to more HPA axis suppression (Table 8).

Table 3 shows the result of ACTH stimulation test and Table 5 and 6 shows serum DHEAS levels during HPA axis suppression.

TABLE 2

Efficacy Analysis: Investigator's Global Assessment (IGA) - Example 5 Vs TEMOVATE ® Cream

| Test drugs | Condition level | Day 1 No. (%) | Day 8 No. (%) | Day 15 No. (%) |
|---|---|---|---|---|
| Example 5 (Number of subjects = 24) | None | 0 (0) | 0 (0) | 0 (0) |
| | Minimal or Almost clear | 0 (0) | 1 (4.2) | 4 (16.7) |
| | Mild | 0 (0) | 6 (25) | 12 (50) |
| | Moderate | 19 (79.2) | 16 (66.7) | 7 (29.2) |
| | Severe/Very Severe | 5 (20.8) | 1 (4.2) | 1 (4.2) |
| TEMOVATE ® (Number of subjects = 22) | None | 0 (0) | 0 (0) | 1 (4.5) |
| | Minimal or Almost clear | 0 (0) | 1 (4.5) | 3 (13.6) |
| | Mild | 0 (0) | 6 (27.3) | 11 (50) |
| | Moderate | 15 (68.2) | 13 (59.1) | 7 (31.8) |
| | Severe/Very Severe | 7 (31.8) | 2 (9.1) | 0 (0) |

TABLE 3

ACTH Stimulation Test Result (Serum Cortisol levels in ug/dL)

| Study Visit: Time Point | Statistics | Example 5 | TEMOVATE ® Cream |
|---|---|---|---|
| Screening: Pre-Stimulation | N | 24 | 22 |
| | Mean ± SD | 11.65 ± 5.392 | 12.43 ± 4.641 |
| | Median | 11.45 | 13.15 |
| Screening: Post-Stimulation | N | 24 | 22 |
| | Mean ± SD | 24.42 ± 2.912 | 26.12 ± 3.938 |
| | Median | 24.3 | 25.3 |
| Day 15: Pre-Stimulation | N | 24 | 22 |
| | Mean ± SD | 10.94 ± 6.247 | 9.11 ± 6.596 |
| | Median | 8.95 | 7.9 |
| Day 15: Post-Stimulation | N | 24 | 22 |
| | Mean ± SD | 23.07 ± 5.942 | 20.38 ± 6.490 |
| | Median | 23.65 | 20 |

TABLE 4

Results of HPA axis suppression (ACTH stimulation test)

| | Example 5 | TEMOVATE ® Cream |
|---|---|---|
| % HPA Suppression* | 12.5 | 36.4 |
| Total Number of Subjects | 24 | 22 |
| Number of Subjects with HPA axis suppression | 3 out of 24 subjects | 8 out of 22 subjects |
| Applied dose (percentage) | 0.025% (w/w) | 0.05% (w/w) |

HPA suppression is considered as cortisol level <=18.00 ug/dL at 30 minutes post stimulation

TABLE 5

Serum DHEAS Concentration (ug/dL)

| Study Visit | Statistics | Example 5 | TEMOVATE ® Cream |
|---|---|---|---|
| Screening | N | 24 | 22 |
| | Mean ± SD | 176.9 ± 97.26 | 135.6 ± 91.51 |
| | Median | 174.5 | 116.5 |
| Day 8 | N | 24 | 22 |
| | Mean ± SD | 169.6 ± 97.68 | 122.9 ± 120.47 |
| | Median | 187.5 | 90 |
| Absolute change from Screening to Day 8 | N | 24 | 22 |
| | Mean ± SD | 7.3 ± 33.20 | 12.7 ± 71.53 |
| | Median | 4 | 24.5 |
| Percent change from Screening to Day 8 | N | 23 | 22 |
| | Mean ± SD | 6.83 ± 28.261 | 19.70 ± 39.739 |
| | Median | 2.53 | 24.77 |
| Day 15 | N | 24 | 22 |
| | Mean ± SD | 148.8 ± 80.31 | 114.7 ± 100.76 |
| | Median | 168.5 | 82 |
| Absolute change from Screening to Day 15 | N | 24 | 22 |
| | Mean ± SD | 28.1 ± 52.73 | 20.9 ± 60.25 |
| | Median | 22 | 26 |
| Percent change from Screening to Day 15 | N | 23 | 22 |
| | Mean ± SD | 11.04 ± 26.966 | 21.62 ± 46.406 |
| | Median | 16.13 | 28.4 |

TABLE 6

Serum DHEAS Concentration (ug/dL) by Subject Status of HPA Axis Suppression

| Study Visit | Statistics | With HPA Axis Suppression | Without HPA Axis Suppression |
|---|---|---|---|
| Day 8 | N | 11 | 35 |
| | Mean ± SD | 111.5 ± 86.83 | 158.5 ± 115.74 |
| | Median | 83 | 130 |
| Absolute change from Screening to Day 8 | N | 11 | 35 |
| | Mean ± SD | 36.3 ± 25.12 | 1.6 ± 58.61 |
| | Median | 34 | 7 |
| Percent change from Screening to Day 8 | N | 11 | 34 |
| | Mean ± SD | 34.72 ± 29.699 | 6.13 ± 33.476 |
| | Median | 29.66 | 9.37 |
| Day 15 | N | 11 | 35 |
| | Mean ± SD | 74.1 ± 61.58 | 150.9 ± 91.97 |
| | Median | 54 | 140 |
| Absolute change from Screening to Day 15 | N | 11 | 35 |
| | Mean ± SD | 73.7 ± 41.62 | 9.2 ± 51.05 |
| | Median | 62 | 20 |
| Percent change from Screening to Day 15 | N | 11 | 34 |
| | Mean ± SD | 54.78 ± 20.228 | 3.73 ± 33.363 |
| | Median | 52.54 | 13.8 |

TABLE 7

Plasma Concentrations of Clobetasol Propionate (pg/mL)

| Visit: Time Point | Statistics | Example 5 | TEMOVATE ® Cream |
|---|---|---|---|
| Screening | N | 24 | 22 |
| | Mean ± SD | 0.000 ± 0.0000 | 2.040 ± 9.5663 |
| | Median | 0 | 0 |
| Day 15: Pre-Treatment (0 hour) | N | 24 | 22 |
| | Mean ± SD | 50.651 ± 96.0016 | 130.735 ± 146.1732 |
| | Median | 27.97 | 81.1 |
| Day 15: 1 Hour | N | 23 | 22 |
| | Mean ± SD | 60.919 ± 142.7070 | 166.949 ± 183.3209 |
| | Median | 31.42 | 115.735 |
| Day 15: 3 Hours | N | 24 | 21 |
| | Mean ± SD | 50.445 ± 71.1675 | 156.968 ± 144.6841 |
| | Median | 28.09 | 128.36 |
| Day 15: 6 Hours | N | 24 | 21 |
| | Mean ± SD | 58.825 ± 99.1553 | 146.324 ± 131.2930 |
| | Median | 30.325 | 125.86 |
| Average of Post-Treatment | N | 22 | 22 |
| | Mean ± SD | 56.339 ± 104.6688 | 152.458 ± 140.8674 |
| | Median | 29.45 | 131.54 |

TABLE 8

Plasma Concentrations of Clobetasol Propionate (pg/mL) by Subject Status of HPA Axis Suppression

| Visit: Time Point | Statistics | With HPA Axis Suppression | Without HPA Axis Suppression |
|---|---|---|---|
| Screening | N | 11 | 35 |
| | Mean ± SD | 0.000 ± 0.0000 | 1.282 ± 7.5844 |
| | Median | 0 | 0 |
| Day 15: Pre-Treatment (0 hour) | N | 11 | 35 |
| | Mean ± SD | 195.691 ± 150.7514 | 55.406 ± 100.3403 |
| | Median | 136.49 | 26.23 |
| Day 15: 1 Hour | N | 11 | 34 |
| | Mean ± SD | 210.873 ± 196.2904 | 81.012 ± 151.2306 |
| | Median | 155.88 | 31.73 |
| Day 15: 3 Hours | N | 11 | 34 |
| | Mean ± SD | 200.668 ± 126.0445 | 67.637 ± 103.9073 |
| | Median | 195.45 | 33.185 |
| Day 15: 6 Hours | N | 11 | 34 |
| | Mean ± SD | 205.386 ± 147.4279 | 65.451 ± 91.5422 |
| | Median | 178.05 | 36.26 |
| Average of Post-Treatment | N | 10 | 34 |
| | Mean ± SD | 217.123 ± 153.7979 | 71.244 ± 106.0424 |
| | Median | 185.565 | 31.74 |

While several particular forms of the application have been illustrated and described, it will be apparent that various modifications and combinations of the application detailed in the text can be made without departing from the spirit and scope of the application.

All publications, patents, and patent applications mentioned in this specification are herein incorporated by reference to the same extent as if each individual publication, patent, or patent application was specifically and individually indicated to be incorporated by reference.

What is claimed is:

1. A method of treating moderate to severe plaque psoriasis in a subject in need thereof comprising topically administering to affected areas of the subject twice daily, for a period of up to two weeks, a topical cream composition comprising 0.025% (w/w) clobetasol, 3% cetostearyl alcohol, 6% of a mixture of glyceryl stearate and PEG 100 stearate, water, 3% diethylene glycol monoethyl ether, 1% white wax, 10% isopropyl myristate, and 5% cyclomethicone, wherein the clobetasol is the only active agent in the composition; and
    wherein treating moderate to severe plaque psoriasis results in an investigator global assessment score of 0 to 1 and no clinically significant hypothalamic pituitary adrenal (HPA) axis suppression.

2. The method of claim 1, wherein the clobetasol is clobetasol propionate.

3. The method of claim 1, wherein the topical cream composition is substantially free of propylene glycol.

4. The method of claim 1, wherein the topical cream composition has a viscosity of from about 0.1 cP to about 500 cP when measured by Brookfield viscometer Cap 2000+ with spindle no. 1 at 530 rpm at 25° C.

5. The method of claim 1, wherein the topical cream composition further comprises an excipient selected from group consisting of polyols, glycols, ethers, glycol ethers, esters, sulfoxides, fatty acids, fatty acid esters, essential oils, terpenes, terpenoids, PEGylated fatty acids, PEGylated fatty acid esters and mixtures thereof nitrogenous compounds, alkanones, organic acids, and combinations thereof, and wherein the glycol is not propylene glycol.

6. The method of claim 1, wherein the topical cream composition further comprises an excipient selected from the group consisting of cetyl alcohol, paraffin, stearyl alcohol, white wax, wax cetyl esters, microcrystalline wax, anionic emulsifying wax, non-ionic emulsifying wax, yellow wax, castor oil, ceresin, cetostearyl alcohol, cyclomethicone, glyceryl behenate, hectorite, myristyl alcohol, cetylstearyl alcohol, triolein, lanolin, and combinations thereof.

7. The method of claim 1, wherein the investigator global assessment score and the mean clobetasol plasma level are measured at day 15.

8. The method of claim 1, wherein treating moderate to severe plaque psoriasis in the subject results in at least 70% of subjects not having hypothalamic pituitary adrenal (HPA) axis suppression.

9. The method of claim 1, wherein treating moderate to severe plaque psoriasis in the subject results in at least 80% of subjects not having hypothalamic pituitary adrenal (HPA) axis suppression.

10. The method of claim 1, wherein treating moderate to severe plaque psoriasis in the subject results in at least 90% of subjects not having hypothalamic pituitary adrenal (HPA) axis suppression.

11. The method of claim 1, wherein the topical cream composition provides a mean clobetasol plasma level less than about 130 pg/mL.

12. The method of claim 1, wherein the topical cream composition provides a mean clobetasol plasma level of less than 150 pg/ml.

13. The method of claim 1, wherein the subject has moderate to severe plaque psoriatic lesions involving at least about 5% body surface area.

14. The method of claim 1, wherein the subject has moderate to severe plaque psoriatic lesions involving at least about 10% body surface area.

15. The method of claim 1, the water is at least 60% of the total weight of the composition.

* * * * *